(12) United States Patent
Philippe et al.

(10) Patent No.: US 6,841,162 B2
(45) Date of Patent: Jan. 11, 2005

(54) COSMETIC OR DERMATOLOGICAL COMPOSITION CONTACTING AT LEAST ONE NATURAL OR RECOMBINANT SPIDER SILK OR AN ANALOG

(75) Inventors: Michel Philippe, Wissous (FR); Jean-Claude Garson, Suresnes (FR); Jean-Pierre Arraudeau, Paris (FR)

(73) Assignee: L'Oreal, Paris (FR)

( * ) Notice: Subject to any disclaimer, the term of this patent is extended or adjusted under 35 U.S.C. 154(b) by 362 days.

(21) Appl. No.: 09/861,597

(22) Filed: May 22, 2001

(65) Prior Publication Data

US 2002/0064539 A1 May 30, 2002

Related U.S. Application Data

(63) Continuation of application No. 09/247,806, filed on Feb. 11, 1999, now Pat. No. 6,280,747.

(30) Foreign Application Priority Data

Feb. 11, 1998 (FR) .............................. 98 01614

(51) Int. Cl.[7] .......................... A61K 7/00; C07K 14/00
(52) U.S. Cl. ...................... 424/401; 530/350; 530/300; 574/2
(58) Field of Search .................. 424/401; 530/350, 530/300; 574/2

(56) References Cited

U.S. PATENT DOCUMENTS

| | | | | |
|---|---|---|---|---|
| 4,839,168 A | * | 6/1989 | Abe et al. ...................... 424/74 |
| 5,756,677 A | | 5/1998 | Lewis et al. |
| 5,965,146 A | * | 10/1999 | Franzke et al. .............. 424/401 |
| 6,268,169 B1 | * | 7/2001 | Fahnestock ................ 435/69.1 |
| 6,280,747 B1 | * | 8/2001 | Phillippe et al. ............. 424/401 |
| 6,296,860 B1 | * | 10/2001 | Hasegawa et al. .......... 424/401 |

FOREIGN PATENT DOCUMENTS

| | | |
|---|---|---|
| EP | 0 452 925 | 10/1991 |
| WO | WO 91/16351 | 10/1991 |
| WO | WO 97/08315 | 3/1997 |

OTHER PUBLICATIONS

Ming Xu, *Structure of a Protein Superfiber: Spider. Dragline Silk*, Proc. Natl. Acad. Sci. USA, vol. 87, pp. 7120–7124, Sep. 1990.

* cited by examiner

Primary Examiner—Karen Cochrane Carlson
(74) Attorney, Agent, or Firm—Oblon, Spivak, McClelland, Maier & Neustadt, P.C.

(57) ABSTRACT

A cosmetic or dermatological composition containing, as an active substance, at least one natural or recombinant spider silk protein, or an analog of such a protein. The composition may be in the form of hair products, skincare products, make-up products or antisun products.

92 Claims, 7 Drawing Sheets

FIGURE 1

```
 1                                   ...       QG A GAAAAAA-GG
 2  A GQG GYG GLG GQG  -   ---  ---  ---  -  ----------
 3  A GQG GYG GLG GQG  A   ---  ---  GQG  A  GAAAAAAAGG
 4  A GQG GYG GLG SQG  A   GRG  ---  GQG  A  GAAAAAA-GG
 5  A GQG GYG GLG SQG  A   GRG  GLG  GQG  A  GAAAAAAAGG
 6  A GQG GYG GLG NQG  A   GRG  ---  GQG  -  --AAAAAGG
 7  A GQG GYG GLG SQG  A   GRG  GLG  GQG  A  GAAAAAA-GG
 8  A GQG GYG GLG GQG  -   ---  ---  ---  -  ----------
 9  A GQG GYG GLG SQG  A   GRG  GLG  GQG  A  GAAAAAAAGG
10  A GQG ---  GLG GQG  A   ---  ---  GQG  A  GASAAAA-GG
11  A GQG GYG GLG SQG  A   GRG  ---  GEG  A  GAAAAAA-GG
12  A GQG GYG GLG GQG  -   ---  ---  ---  -  ----------
13  A GQG GYG GLG SQG  A   GRG  GLG  GQG  A  GAAAA---GG
14  A CQG ---  GLG GQG  A   ---  ---  GQG  A  GAAAAAA-GG
15  A GQG GYG GLG SQG  A   GRG  GLG  GQG  A  GAVAAAAAGG
16  A GQG GYG GLG SQG  A   GRG  ---  GQG  A  GAAAAAA-GG
17  A GQR GYG GLG NQG  A   GRG  GLG  GQG  A  GAAAAAAGG
18  A GQG GYG GLG NQG  A   GRG  ---  GQG  -  --AAAA-GG
19  A GQG GYG GLG SQG  A   GRG  ---  GQG  A  GAAAAAA-VG
20  A GQG ---  GIR GQG  -   ---  ---  ---  -  ----------
21  A GQG GYG GLG SQG  S   GRG  GLG  GQG  A  GAAAAAA-GG
22  A GQG ---  GLG GQG  A   ---  ---  GQG  A  GAAAAAA-GG
23  V RQG GYG GLG SQG  A   GRG  ---  GQG  A  GAAAAAA-GG
24  A GQG GYG GLG GQG  V   GRG  GLG  GQG  A  GAAAA---GG
25  A GQG GYG GVG S--  -   ---  ---  --G  A  SAASAAAA--
```

FIGURE 2

```
            ...PGGY GPGQQ GPGGY GPGQQ GP--SGPGS AAAAPAAAAA
GPGGY GPGQQ GPGGY GPGQQ GPGRY GPGQQ GP--SGPGS AAAAAA----
-----.GSGQQ GPGGY GPRQQ GPGGY GQGQQ GP--SGPGS AAAASAAASA ESGQQ
GPGGY GPGQQ GPGGY GPGQQ GPGGY GPGQQ GP--SGPGS AAAAAAAAS-
----- GPGQQ GPGGY GPGQQ GPGGY GPGQQ GP--SGPGS AAAAAAAAS-
----- GPGQQ GPGGY GPGQQ GPGGY GPGQQ GL--SGPGS AAAAAAA---
----- ----- ----- GPGQQ GPGGY GPGQQ GP--SGPGS AAAAAAAAA-
----- ----- GPGGY GPGQQ GPGGY GPGQQ GP--SGAGS AAAAAA----
----- GPGQQ GLGGY GPGQQ GPGGY GPGQQ GPGGYGPGS ASAAAAAA--
----- ----- ----- GPGQQ GPGGY GPGQQ GP--SGPGS ASAAAAAAAA
----- ----- GPGGY GPGQQ GPGGY APGQQ GP--SGPGS ASAAAAAAAA
----- ----- GPGGY GPGQQ GPGGY APGQQ GP--SGPGS AAAAAASA-
----- ----- ----- ----- GPGGY GPAQQ GP--SGPGI AASAASA---
----- ----- ----- ----- GPGGY GPAQQ GPAGYGPGS AVAASA----
----- ----- ----- ----- ----- ---GA GSAGYGPGS QASAAAS---
```

FIGURE 3

```
GAAGAGGYGRGAG--------------GYGGQGGYGAGAGAGAAAAA
GAGAGGAGGYGRGAGAGAGAAAGAGAGGAGYGGQGGYGAGAGAGAAAAA
GAGAGGAGGYGRGAGAGAGAAAGAGA----GGYGGQGGYGAGAGAGAAAAAA
GAGSGGAGGYGRGAGAGAGAAAGAGAGA--GSYGGQGGYGAGAGAGAAAAA
GAGAGGAGGYGRGAGAGAGAGAGAAARAGAGAGG-------------AAAAA
GAGAGGAGGYGRGAGAGAGAAAGAGAGA------GGYGGQSGYGAGAG--AAAAA
GAGAGGAGGYGRGAGAGAGAAAGAGAGAAAGAGAGGYGGQGGYGAGAGAGAAAAA
GAGAGGAGGYGRGAGAGAGAAAGAGAG----GYGGQGGYGAGAGAGAAAAA
-TGAGGAGGYGRGAGAGAGAAAGAGAGTGGAGYGGQGGYGAGAGAGAAAAA
GAGAGGAG-YGRGAGAGAGAAAGAGAGAAAGAGAGAGGYGGQGGYGAGARAGAAAAA
GAGAGGAAGYSRGGRAGAAGAGAGAAAGAGAGAGGYGGQGGYGAGAGAGAAAAA
GAGSGGAGGYGRGAGAGAAAGAGAAAGAGAGAGGYGGQGGYGAGAGAAAAA
GAGAGRGGYGRGAGAGGYGGQGGYGAGAGAGAAAAA
```

FIGURE 4A

Monomère :

```
                       G  AGRG---GQGAGAAAAAA-GG
AGQGGYGGLGSQG             AGRGGLGGQGAGAAAAAAGG
AGQGG---LGSQG             A------GQGAGAAAAAA-GG
AGQGGYGGLGSQG             --------------------
AGQGGYGGLGSQ
```

FIGURE 4B

Polymère :

```
-                      G  AGRG---GQGAGAAAAAA-GG
AGQGGYGGLGSQG             AGRGGLGGQGAGAAAAAAGG
AGQGG---LGSQG             A------GQGAGAAAAAA-GG
AGQGGYGGLGSQG             --------------------
AGQGGYGGLGSQG             AGRG---GQGAGAAAAAA-GG
AGQGGYGGLGSQG             AGRGGLGGQGAGAAAAAAGG
AGQGG---LGSQG             A------GQGAGAAAAAA-GG
AGQGGYGGLGSQG             --------------------
AGQGGYGGLGSQG             AGRG---GQGAGAAAAAA-GG
AGQGGYGGLGSQG             AGRGGLGGQGAGAAAAAAGG
AGQGG---LGSQG             A------GQGAGAAAAAA-GG
AGQGGYGGLGSQG             --------------------
AGQGGYGGLGSQG             AGRG---GQGAGAAAAAA-GG
AGQGGYGGLGSQG             AGRGGLGGQGAGAAAAAAGG
AGQGG---LGSQG             A------GQGAGAAAAAA-GG
AGQGGYGGLGSQG             --------------------
AGQGGYGGLGSQG             AGRG---GQGAGAAAAAA-GG
AGQGGYGGLGSQG             AGRGGLGGQGAGAAAAAAGG
AGQGG---LGSQG             A------GQGAGAAAAAA-GG
AGQGGYGGLGSQG             --------------------
AGQGGYGGLGSQG             AGRG---GQGAGAAAAAA-GG
AGQGGYGGLGSQG             AGRGGLGGQGAGAAAAAAGG
AGQGG---LGSQG             A------GQGAGAAAAAA-GG
AGQGGYGGLGSQG             --------------------
AGQGGYGGLGSQ
```

FIGURE 5A

Monomère :

```
            SQG              -------------------
AGQGGYGGLGSQG    AGRGGLGGQGAGAAAAAAGG
AGQGG---LGSQG    A------GQGAGAAAAA-GG
AGQGGYGGLGSQG    AGRG---GQGAGAAAAA-GG
AGQGGYGGLG
```

FIGURE 5B

Polymère :

```
            SQG              -------------------
AGQGGYGGLGSQG    AGRGGLGGQGAGAAAAAAGG
AGQGG---LGSQG    A------GQGAGAAAAA-GG
AGQGGYGGLGSQG    AGRG---GQGAGAAAAA-GG
AGQGGYGGLGSQG    -------------------
AGQGGYGGLGSQG    AGRGGLGGQGAGAAAAAAGG
AGQGG---LGSQG    A------GQGAGAAAAA-GG
AGQGGYGGLGSQG    AGRG---GQGAGAAAAA-GG
AGQGGYGGLGSQG    -------------------
AGQGGYGGLGSQG    AGRGGLGGQGAGAAAAAAGG
AGQGG---LGSQG    A------GQGAGAAAAA-GG
AGQGGYGGLGSQG    AGRG---GQGAGAAAAA-GG
AGQGGYGGLGSQG    -------------------
AGQGGYGGLGSQG    AGRGGLGGQGAGAAAAAAGG
AGQGG---LGSQG    A------GQGAGAAAAA-GG
AGQGGYGGLGSQG    AGRG---GQGAGAAAAA-GG
AGQGGYGGLGSQG    -------------------
AGQGGYGGLGSQG    AGRGGLGGQGAGAAAAAAGG
AGQGG---LGSQG    A------GQGAGAAAAA-GG
AGQGGYGGLGSQG    AGRG---GQGAGAAAAA-GG
AGQGGYGGLGSQG    -------------------
AGQGGYGGLGSQG    AGRGGLGGQGAGAAAAAAGG
AGQGG---LGSQG    A------GQGAGAAAAA-GG
AGQGGYGGLGSQG    AGRG---GQGAGAAAAA-GG
AGQGGYGGLG
```

FIGURE 6A

Monomère :

```
                G  -------------------
AGQGGYGGLGSQG   AGRGGLGGQGAGAAAAAAGG
AGQGG---LGSQG   A------GQGAGAAAAA-GG
AGQGGYGGLGSQG   AGRG---GQGAGAAAAA-GG
AGQGGYGGLGSQ
```

FIGURE 6B

Polymère :

```
                G  --------------------
AGQGGYGGLGSQG   AGRGGLGGQGAGAAAAAAGG
AGQGG---LGSQG   A------GQGAGAAAAA-GG
AGQGGYGGLGSQG   AGRG---GQGAGAAAAA-GG
AGQGGYGGLGSQG   -------------------
AGQGGYGGLGSQG   AGRGGLGGQGAGAAAAAAGG
AGQGG---LGSQG   A------GQGAGAAAAA-GG
AGQGGYGGLGSQG   AGRG---GQGAGAAAAA-GG
AGQGGYGGLGSQG   -------------------
AGQGGYGGLGSQG   AGRGGLGGQGAGAAAAAAGG
AGQGG---LGSQG   A------GQGAGAAAAA-GG
AGQGGYGGLGSQG   AGRG---GQGAGAAAAA-GG
AGQGGYGGLGSQG   -------------------
AGQGGYGGLGSQG   AGRGGLGGQGAGAAAAAAGG
AGQGG---LGSQG   A------GQGAGAAAAA-GG
AGQGGYGGLGSQG   AGRG---GQGAGAAAAA-GG
AGQGGYGGLGSQG   -------------------
AGQGGYGGLGSQG   AGRGGLGGQGAGAAAAAAGG
AGQGG---LGSQG   A------GQGAGAAAAA-GG
AGQGGYGGLGSQG   AGRG---GQGAGAAAAA-GG
AGQGGYGGLGSQG   -------------------
AGQGGYGGLGSQG   AGRGGLGGQGAGAAAAAAGG
AGQGG---LGSQG   A------GQGAGAAAAA-GG
AGQGGYGGLGSQG   AGRG---GQGAGAAAAA-GG
AGQGGYGGLGSQ
```

FIGURE 7A

Monomère :

```
                                            |GP--SGPGS AAAAAA----
----- GPGQQ|GPGGY GPGQQ GPGGY GPGQQ|GP--SGPGS AAAAAAA--
----- ----- GPGGY|GPGQQ GPGGY GPGQQ|GP--SGPGS AAAAAAAA-
GPGGY|GPGQQ GPGGY GPGQQ GPGGY GPGQQ|
```

FIGURE 7B

Polymère :

```
                                            |GP--SGPGS AAAAAA----
----- GPGQQ|GPGGY GPGQQ GPGGY GPGQQ|GP--SGPGS AAAAAAA--
----- ----- GPGGY|GPGQQ GPGGY GPGQQ|GP--SGPGS AAAAAAAA-
GPGGY|GPGQQ GPGGY GPGQQ GPGGY GPGQQ|GP--SGPGS AAAAA----
----- GPGQQ|GPGGY GPGQQ GPGGY GPGQQ|GP--SGPGS AAAAAAA--
----- ----- GPGGY|GPGQQ GPGGY GPGQQ|GP--SGPGS AAAAAAAA-
GPGGY|GPGGY·GPGQQ GPGGY GPGQQ|GP--SGPGS AAAAAA----
----- GPGQQ|GPGGY GPGQQ GPGGY GPGQQ|GP--SGPGS AAAAAAA--
----- ----- GPGGY|GPGQQ GPGGY GPGQQ|GP--SGPGS AAAAAAAA-
GPGGY|GPGQQ GPGGY GPGQQ GPGGY GPGQQ|GP--SGPGS AAAAAA----
----- GPGQQ|GPGGY GPGQQ GPGGY GPGQQ|GP--SGPGS AAAAAAA--
----- ----- GPGGY|GPGQQ GPGGY GPGQQ|GP--SGPGS AAAAAAAA-
GPGGY|GPGQQ GPGGY GPGQQ GPGGY GPGQQ|GP--SGPGS AAAAAA----
----- GPGQQ|GPGGY GPGQQ GPGGY GPGQQ|GP--SGPGS AAAAAAA--
----- ----- GPGGY|GPGQQ GPGGY GPGQQ|GP--SGPGS AAAAAAAA-
GPGGY|GPGQQ GPGGY GPGQQ GPGGY GPGQQ|GP--SGPGS AAAAAA----
----- GPGQQ|GPGGY GPGQQ GPGGY GPGQQ|GP--SGPGS AAAAAAA--
----- ----- GPGGY|GPGQQ GPGGY GPGQQ|GP--SGPGS AAAAAAAA-
GPGGY|GPGQQ GPGGY GPGQQ GPGGY GPGQQ|
```

COSMETIC OR DERMATOLOGICAL COMPOSITION CONTACTING AT LEAST ONE NATURAL OR RECOMBINANT SPIDER SILK OR AN ANALOG

This application is a Continuation of U.S. application Ser. No. 09/247,806, filed on Feb. 11, 1999, now U.S. Pat. No. 6,280,747.

BACKGROUND OF THE INVENTION

1. Field of the Invention

The present invention relates to a novel cosmetic or dermatological composition containing, as an active substance, at least one natural or recombinant spider silk protein, or an analog of such a protein. More particularly, the present invention relates to compositions in the form of hair products, skincare products, make-up products or antisun products based on a spider silk protein.

2. Discussion of the Background Art

The use of natural or plant proteins is well known and has been widely practiced in the cosmetics field, in particular the use of silk proteins from the insect Bombyx mori, more particularly described in Biomaterials Ed. D. Byrom, Stocktompress, 1–54, (1991). However, these silk proteins do not have good mechanical properties in the form of threads or films and cannot therefore satisfactorily fulfill their functions as film-forming agents.

Spider silk proteins have been characterized by Lucas et al., Adv. Protein Chem. 13:107–242, (1958); Andersen, Comp. Became. Physiol. 35:705–711, (1970); Denny M W, J. Exp. Biol., 65, 483–506, (1976); and Lucas F, Discovery, 25, 20–26, (1964). They are known for their good mechanical and elastic properties.

SUMMARY OF THE INVENTION

It has now been discovered that, in addition to their known properties, spider silk proteins give cosmetic or dermatological compositions unexpected properties, in particular enhancement of the moisturizing or plasticizing effect. Spider silk proteins moreover behave as good water-resistant film-forming agents, and especially have a low surface density.

Accordingly, it is an object of the present invention to provide a cosmetic or dermatological composition containing an effective amount of at least one natural or recombinant spider silk protein, or an analog of such a protein.

Various other objects, features and attendant advantages of the present invention will be more fully appreciated as the same becomes better understood from the following detailed description when considered in connection with the accompanying Figures.

BRIEF DESCRIPTION OF THE FIGURES

FIG. 1: The peptide sequence of a natural spider silk protein, Spidroin major 1 (SEO ID NO:1). The "-" are added to show the alignment of the repeating units.

FIG. 2: The peptide sequence of a natural spider silk protein, Spidroin major 2 (SEQ ID NO:2). The "-" are added to show the alignment of the repeating units.

FIG. 3: The peptide sequence corresponding to residues 92 to 706 of the natural spider silk protein. Spidroin minor 1 (SEQ ID NO:1). The "-" are added to show the alignment of the repeating units.

FIGS. 4A–B: The amino acid sequence of a monomer (SEQ ID NO:3) and of a polymer (SEQ ID NO:4) of a Spidroin major 1 analog.

FIGS. 5A–B: The amino acid sequence of a monomer (SEQ ID NO: 5) and of a polymer (SEQ ID NO: 6) of a Spidroin major 1 analog.

FIGS. 6A–B: The amino acid sequence of a monomer (SEQ ID NO:7) and of a polymer (SEQ ID NO:8) of a Spidroin major 1 analog.

FIGS. 7A–B: The amino acid sequence of a monomer (SEQ ID NO:9) and of a polymer (SEQ ID NO:10) of a Spidroin major 2 analog.

DETAILED DESCRIPTION OF THE INVENTION

According to one specific embodiment of the cosmetic compositions according to the present invention, the spider silk proteins are preferably recombinant spider silk proteins.

Although natural proteins can be used according to the invention for the formulation of cosmetic or dermatological products, in particular on account of their good biocompatibility and biodegradability, the genes coding for these silk proteins have a certain level of genetic instability due to the repetitions in the nucleotide sequences, which does not make it possible to obtain good reproducibility of their physicochemical properties.

In contrast, recombinant spider silk proteins have the advantage of having a predetermined peptide sequence which can be designed as a function of the physicochemical properties of strength, or alternatively of elasticity, required for the various cosmetic or dermatological applications desired.

According to the invention, the compositions can contain, in an effective amount, at least one natural or recombinant spider silk protein, corresponding to Spidroin major 1 described by Xu et al., PNAS, USA, 87, 7120, (1990), to Spidroin major 2 described by Hinman and Lewis, J. Biol. Chem., 267, 19320, (1922), or alternatively to the minor Spidrions described in patent application WO 95/25165. The peptide sequences are recited FIGS. 1 to 3 of the present patent application. Each of the above-cited references is incorporated herein by reference in its entirety.

When the compositions according to the present invention contain at least one recombinant spider silk protein, this protein comprises a repeating unit of amino acids corresponding to one of the sequences (I), (II), (III) and/or (IV) below.

The following abbreviations are used to identify the amino acids:

| Amino acids | Abbreviations |
| --- | --- |
| Alanine | A |
| Glycine | G |
| Proline | P |
| Serine | S |
| Glutamine | Q |
| Tyrosine | Y |
| Arginine | R |
| Asparagine | N |
| Aspartic acid | D |
| Cysteine | C |
| Glutamic acid | E |
| Histidine | H |
| Leucine | L |
| Lysine | K |
| Methionine | M |
| Phenylalanine | F |
| Threonine | T |

-continued

| Amino acids | Abbreviations |
|---|---|
| Tryptophan | W |
| Valine | V |
| Isoleucine | I |

$$[(XGG)_w(XGA)(GXG)_x(AGA)_y(G)_zAG]_p \text{ (SEQ ID NO: 11)} \quad \text{(I)}$$

in which:
X corresponds to tyrosine or to glutamine,
w is an integer equal to 2 or 3,
x is an integer from 1 to 3,
y is an integer from 5 to 7,
z is an integer equal to 1 or 2, and
p is an integer such that the molecular weight of the protein is between 10 and 400 kDa, and/or $$[(GPG_2YGPGQ_2)_a(X')_2S(A)_b]_p \text{ (SEQ ID NO: 12)} \quad \text{(II)}$$

in which:
X' corresponds to the amino acid sequence GPS or GPG,
a is equal to 2 or 3,
b is an integer from 7 to 10, and
p is an integer such that the molecular weight of the protein is between 10 and 400 kDa, and/or $$[(GR)(GA)_l(A)_m(GGX'')_n(GA)_l(A)_m]_p \text{ (SEQ ID NO:13)} \quad \text{(III)}$$

and/or $$[(GGX'')_n(GA)_m(A)_l]_p \text{ (SEQ ID NO:14)}$$

in which:
X" corresponds to tyrosine, glutamine or alanine,
l is an integer from 1 to 6,
m is an integer from 0 to 4,
n is an integer from 1 to 4, and
p is an integer such that the molecular weight of the protein is between 10 and 400 kDa.

According to another embodiment of the present invention, the cosmetic or dermatological compositions can contain an effective amount of at least one analog of a spider silk protein.

According to the invention, the term "analog" refers to peptides which imitate the repeating units of amino acids derived from natural spider silk proteins and the profile of variation between the repeating units without modifying their three-dimensional conformation. It is thus possible to design a peptide sequence so as to obtain the physicochemical properties required for the various cosmetic or dermatological applications desired.

In this respect, patent applications WO 91/16351 and EP 452,925, each incorporated herein by reference, describe the synthesis of peptide analogs with elasticity properties which are enhanced on account of the elongation of the polyalanine sequence. Conversely, it is possible to reduce the elasticity of the protein by removing the polyalanine sequences. Similarly, when it is desired to obtain a less rigid protein, its suffices to replace the glycine residues with serine residues.

Moreover, patent application WO 94/29450, incorporated herein by reference, describes the synthesis of peptide analogs containing preferred codons which are specific for the host organism. The reason for this is that it is well known that the expression of foreign genes is more effective when the codon of preferred use by the organism is used. Such peptide analogs can be synthesized from DNA monomers of 300 to 400 bp coding for one or more amino acid repeating units, which are then combined to form a complete gene coding for an analog. Examples of peptide analog sequences are given in FIGS. 4–7.

Various methods for synthesizing these peptide analogs are known and have been described by Ausubel et al., Current Protocols in Molecular Biology § 8 (John Wiley & Sons 1987, (1990)), incorporated herein by reference. This involves, inter alia, site-directed mutagenesis of polynucleotides coding for a functional fragment of a spider silk protein.

The natural spider silk proteins can be harvested according to the method described by Work et al., J. Arachnol., 10,1–10, (1982) and in patent application EP 452,925. Both of these references are incorporated herein by reference.

The recombinant proteins can be produced by transformed prokaryotic or eukaryotic systems containing the cDNA coding for a spider silk protein, for a fragment of this protein or for an analog of such a protein.

The systems for expressing proteins are well known and have been described by Maniatis, Molecular Cloning, A Lab Manual (1982) and Sambrook et al., Molecular Cloning, volumes 1, 2, 3 (Cold Spring Harbor Laboratory: Cold Spring Harbor, N.Y., (1989)). Both of these references are incorporated herein by reference.

The prokaryotic systems include Gram-negative bacteria or Gram-positive bacteria, such as *Escherichia coli* or *Bacillus subtilis*. The prokaryotic expression vectors can include an origin of replication which can be recognized by the host organism, a homologous or heterologous promoter which is functional in the said host, the DNA sequence coding for the spider silk protein, for a fragment of this protein or for an analogous protein, and a selection gene such as an antibiotic-resistance gene.

The eukaryotic systems include yeasts (*Saccharomyces cerevisiae*) and insect, mammalian or plant cells. In this case, the expression vectors can include a yeast plasmid origin of replication or an autonomous replication sequence, a promoter, a DNA sequence coding for a spider silk protein, for a fragment or for an analogous protein, a polyadenylation sequence, a transcription termination site and, lastly, a selection gene.

In the compositions of the invention, the expression "effective amount" of at least one natural or recombinant spider silk protein, or of an analog, corresponds to a proportion of from about $10^{-4}$ to about 30% by weight, but preferably from $10^{-3}$ to 15% by weight, relative to the total weight of the composition, it being possible for this proportion to vary as a function of the type of cosmetic or dermatological composition. These ranges include all specific values and subranges therebetween, such as $10^{-2}$, 0.1, 0.2, 0.5, 1, 2, 5, 10, 20 and 25% by weight.

According to a first specific embodiment, the compositions according to the invention are anhydrous and comprise a fatty phase in a proportion generally of from about 10 to about 90% by weight relative to the total weight of the composition, where the fatty phase containing at least one liquid, solid or semi-solid fatty substance. This range for the fatty phase includes all specific values and subranges therebetween, such as 20, 30, 40, 50, 60, 70 and 80% by weight.

The fatty substances can be chosen from oils, waxes, gums and/or so-called pasty fatty substances.

A—The oils in the fatty phase can be of mineral, animal, plant or synthetic origin, and may or may not be volatile at room temperature.

Oils of mineral origin which may be mentioned in particular are liquid paraffin and liquid petroleum jelly.

Oils of animal origin which may be mentioned in particular are squalene and squalane.

Oils of plant origin which may be mentioned in particular are sweet almond oil, beauty-leaf oil, palm oil, avocado oil, jojoba oil, sesame oil, olive oil, castor oil and cereal germ oils such as, for example, wheatgerm oil.

Synthetic oils which may be mentioned in particular are:

(1) esters of the following formula:

$$R_1\text{—COOR}_2$$

in which:

$R_1$ represents a higher fatty acid residue containing from 7 to 20 carbon atoms, and $R_2$ represents a hydrocarbon-based radical containing from 3 to 30 carbon atoms.

These ranges of carbon numbers include all specific valves therebetween.

Among these esters, mention may be made in particular of: purcellin oil, butyl myristate, isopropyl myristate, cetyl myristate, isopropyl palmitate, butyl stearate, hexadecyl stearate, isopropyl stearate, octyl stearate, isocetyl stearate, decyl oleate, hexyl laurate, isononyl isononanoate and esters derived from lanolic acid, such as isopropyl lanolate and isocetyl lanolate.

Other synthetic oils which may also be mentioned are isododecane, isohexadecane, polyisobutenes and hydrogenated polyisobutene, as well as acetylglycerides, octanoates and decanoates of polyalcohols such as those of glycol and of glycerol, ricinoleates of alcohols or of polyalcohols, such as cetyl ricinoleate, propylene glycol dicaprylate and diisopropyl adipate;

(2) fatty alcohols such as oleyl alcohol, linoleyl alcohol, linolenyl alcohol, isostearyl alcohol and octyldodecanol;

(3) silicone oils such as optionally functionalized linear polydiorganosiloxanes, cyclic polydiorganosiloxanes and in particular cyclotetra- and -pentadimethicones and organopolysiloxanes such as alkyl, alkoxy or phenyl dimethicones, and in particular phenyltrimethicone;

(4) fluoro oils such as perfluoroalkanes and perfluoropolyethers and partially fluorinated hydrocarbon-based oils.

B—The waxes in the fatty phase can be of mineral, fossil, animal, plant or synthetic origin or alternatively can be hydrogenated oils or fatty esters which are solid at 25° C.

Among the mineral waxes, mention may be made in particular of microcrystalline waxes, paraffin, petroleum jelly and ceresine.

Among the fossil waxes, mention may be made of ozocerite and montan wax.

Among the waxes of animal origin, mention may be made of beeswax, spermaceti, lanolin wax and derivatives obtained from lanolin such as lanolin alcohols, hydrogenated lanolin, hydroxylated lanolin, acetylated lanolin, lanolin fatty acids and acetylated lanolin alcohol.

Among the waxes of plant origin, mention may be made in particular of candelilla wax, carnauba wax, Japan wax and cocoa butter.

Among the synthetic waxes, mention may be made in particular of ethylene homopolymers and copolymers of ethylene and of a monomer corresponding to the formula:

$$CH_2=CH\text{—}R_3$$

in which:

$R_3$ represents an alkyl radical containing from 1 to 30 carbon atoms or an aryl or aralkyl radical.

The alkyl radical of 1 to 30 carbon atoms is preferably a methyl, ethyl, propyl, isopropyl, butyl, decyl, dodecyl or octadecyl radical.

Waxes obtained by Fisher-Tropsch synthesis and silicone waxes can also be used.

Among the hydrogenated oils which are solid at 25° C., mention may be made in particular of hydrogenated castor oil, hydrogenated palm oil, hydrogenated tallow and hydrogenated coconut oil.

Among the fatty esters which are solid at 25° C., mention may be made in particular of propylene glycol monomyristate and myristyl myristate.

As waxes which can be used in the compositions according to the invention, mention may also be made of cetyl alcohol, stearyl alcohol, mono-, di- and triglycerides which are solid at 25° C., stearic monoethanolamide, colophony and its derivatives such as glycol abietate and glyceryl abietate, sucroglycerides and calcium, magnesium, zinc and aluminium oleates, myristates, lanolates, stearates and dihydroxystearates.

C—The pasty-type fatty substances can be of mineral, animal, plant or synthetic origin.

Among the pasty fatty substances, mention may be made in particular of synthetic esters such as arachidyl propionate, polyvinyl laurate, polyethylene waxes and organopolysiloxanes such as alkyldimethicones, alkoxydimethicones or dimethicone esters.

Needless to say, the anhydrous compositions according to the invention can also contain one or more conventional cosmetic or dermatological additives or adjuvants.

These anhydrous compositions can be in various forms such as, in particular, in the form of an oily gel, solid products, such as compacted or cast powders, or alternatively sticks such as, for example lipsticks.

When the compositions according to the invention are in the form of an oily gel, they generally contain, besides the constituents defined above, an oily gelling agent.

Among the oily gelling agents, mention may be made in particular of metal esters such as polyoxyaluminium stearate and aluminium or magnesium hydroxystearate, fatty acid esters of glycol, triglycerides, mixtures of fatty alcohols, cholesterol derivatives and in particular hydroxycholesterol, and clay minerals which swell in the presence of oil, and in particular those belonging to the montmorillonite group.

The oily gelling agents can be present in a very variable proportion depending on the desired texture of the compositions. However, in most cases, they are present in a proportion of from about 0.1 to about 30% by weight relative to the total weight of the composition. This range includes all specific values and subranges therebetween, such as 0.2, 0.5, 1, 2, 5, 10, 15, 20 and 25% by weight.

These anhydrous compositions according to the invention can be used in particular as care, cleansing or make-up products.

When they are present in the form of make-up products, they can be, in particular, foundations, mascaras, eyeliners, lipsticks, eyeshadows or blushers. These compositions are generally colored and, in this case, contain, as cosmetic adjuvants, dyes and/or pigments which are well known in the field of make-up products.

According to a second embodiment, the compositions according to the invention are stable dispersions in the form of a water-in-oil (W/O) or oil-in-water (O/W) emulsion, which consist essentially (i) of a fatty phase in a proportion of from about 0.1 to about 50% by weight relative to the total weight of the composition, the said fatty phase containing at least one natural or recombinant spider silk protein, or an analog, in a proportion of from about $10^{-4}$ to about 30% by weight relative to the total weight of the emulsion, (ii) of an aqueous phase in a proportion of from about 50 to about 98.9% by weight relative to the total weight of the emulsion, and (iii) of at least one emulsifier in a proportion of from about 1 to about 10% by weight relative to the total weight of the emulsion.

The ranges specified for components (i)–(iii) above include all specific values and subranges therebetween.

These emulsions, which are in the form of creams, have a good film-forming nature and give a very satisfactory comfortable sensation after they have been applied. Such emulsions can be used as care, cleansing or make-up products.

When these compositions are skincare products, they can be, in particular, anti-wrinkle products for improving the appearance of the skin relief.

When these compositions are make-up products, they can be, in particular, foundations or mascaras containing, in this case, a certain proportion of pigments and/or dyes.

According to a third embodiment of the compositions according to the invention, they are in the form of products for the nails such as nail varnishes or nailcare products.

According to this embodiment, the compositions are preferably in the form of nail varnishes containing:

(i) a solvent system for varnishes, and (ii) a film-forming substance.

The natural or recombinant spider silk protein or analog is, according to this embodiment, generally in a proportion of from $10^{-4}$ to 30% by weight relative to the total weight of the varnish.

According to this embodiment, the solvent system for the varnish is generally present in a proportion ranging from 55 to 90% by weight relative to the total weight of the varnish. This range includes all specific values and subranges therebetween, including 60, 65, 70, 75, 80, and 85% by weight.

Although the solvent system can be of the aqueous type, it preferably consists of a mixture of various volatile organic solvents, in order to obtain relatively short drying times.

Among these solvents, mention may be made of acetone, ethyl acetate, butyl acetate, 2-methoxyethyl acetate, methyl ethyl ketone, methyl isobutyl ketone, methyl acetate, amyl acetate and isopropyl acetate.

The solvent system can also comprise a diluent which is preferably a saturated, linear or branched hydrocarbon, such as hexane or octane, or alternatively an aromatic hydrocarbon such as toluene or xylene, in a proportion of from about 10 to about 35% by weight relative to the total weight of the varnish. This range includes all specific values and subranges therebetween, including 15, 20, 25 and 30% by weight. The solvent system can also include other volatile solvents such as ethanol, n-butanol, n-propanol, isopropanol or mixtures thereof.

Besides the spider silk protein, the composition according to the invention can also comprise a film-forming substance. This film-forming substance is generally present in a proportion of from about 5 to about 35% by weight relative to the total weight of the varnish. This range includes all specific values and subranges therebetween, including 10, 15, 20, 25, and 30% by weight. Among these film-forming substances, mention may be made of nitrocelluloses of the "RS" or "SS" type, in particular ¼ second RS type nitrocellulose, ¼ second RS type nitrocellulose, ½ second SS type nitrocellulose and ¾ second RS type nitrocellulose. Film-forming substances which can also be used according to the invention are polyvinyl derivatives such as polyvinyl butyrate.

Other film-forming substances which can be used according to the invention are cellulose derivatives other than nitrocellulose, acrylic polymers or copolymers, acrylic, styrene, acrylate-styrene and vinyl resins, vinyl copolymers, polyester polymers, arylsulphonamide resins and alkyde resins.

The varnishes according to the invention can also contain a plasticizer, which is generally present in a proportion of from about 5 to about 20% by weight relative to the total weight of the varnish. This range includes all specific values and subranges therebetween, including 10, 12, 15 and 18% by weight. The plasticizers allow the flexibility of the film to be adjusted without reducing its strength or its physical force. Among the plasticizers, mention may be made of: tricresyl phosphate, benzyl benzoate, tributyl phosphate, butyl acetyl ricinoleate, triethyl citrate, tributyl acetyl citrate, dibutyl phthalate and camphor.

The products for nails according to the invention can be either colorless or colored. When they are colored, they then contain pigments and/or dyes which are well known in the nail varnish sector.

According to a final specific embodiment of the cosmetic compositions according to the invention, they are hair compositions containing, in a suitable cosmetic vehicle, a natural or recombinant spider silk protein or an analog, in a proportion of from about $10^{-4}$ to about 30% by weight relative to the total weight of the composition.

These hair compositions can be aqueous, alcoholic or aqueous-alcoholic solutions, the alcohol preferably being ethanol or isopropanol, in a proportion of from about 60 to about 99.5% by weight relative to the total weight, for the aqueous-alcoholic solutions. This range includes all specific values and subranges therebetween, including 65, 70, 75, 80, 85, 90, 95 and 98% by weight.

These hair compositions can be in the form of lotions, aerosols, gels, mousses or fixing shampoos. They can be applied easily to the hair and form a hydrophobic film of low density at the surface of the hair, allowing satisfactory shaping of the hairstyle without making the hair feel sticky.

On account of the deposition of a thin hydrophobic film on the skin, the hair or the nails, the compositions according to the invention, as have just been described above, allow the vectorization of various active agents which are generally difficult to apply, such as vitamins, hormones, moisturizers and products which are active against skin or hair disorders.

The compositions according to the invention can also contain one or more conventional cosmetic adjuvants, such as antioxidants, preserving agents, fillers, surfactants, UVA and/or UVB sunscreens, fragrances, thickeners, wetting agents and anionic, nonionic or amphoteric polymers.

Among these adjuvants, the fillers are generally present, in the make-up or care products or in the dermatological products, in a maximum proportion of about 99.9% by weight relative to the total weight of the composition.

These fillers, in the form of very fine powders, can be of natural or synthetic origin. Among these, mention may be made in particular of:

a) mineral powders such as talc, kaolin, mica, silica, silicates, alumina, zeolites, hydroxyapatite, sericite, titanium dioxide, titanium micas, barium sulphate, bismuth oxychloride, boron nitride and metal powders such as aluminium powder;

b) plant powders such as corn starch, wheat starch or rice starch powders;

c) organic powders such as nylon powder, polyamide powder, polyester powder, polytetrafluoroethylene powder or polyethylene powder.

These various powders can also be coated, for example with metal salts of fatty acids, amino acids, lecithin, collagen, silicone compounds, fluoro compounds or with any common coating agent.

Besides the fillers, dyes and pigments also form part of the anhydrous make-up compositions or compositions in the form of dispersions. The compositions of the invention make it possible, by coating, to improve the water-resistance properties of these fragile compounds. The dyes and/or pigments are generally present in a maximum proportion of about 40% relative to the total weight of the composition.

In the lipsticks, the proportion of at least one dye and/or pigment is generally of from about 0.1 to about 15% by weight relative to the total weight of the lipstick.

Among the dyes in the make-up products, and in particular in the lipsticks, mention may be made of eosin derivatives such as D&C Red No. 21 and halogenated fluorescein derivatives such as D&C Red No. 27, D&C Red Orange No. 5 in combination with D&C Red No. 21 and D&C Orange No. 10.

Among the pigments, which may be inorganic or organic or alternatively metal lakes, mention may be made of titanium dioxide, zinc oxide, D&C Red No. 36 and D&C Orange No. 17, the calcium lakes of D&C Red Nos.7, 11, 31 and 34, the barium lake of D&C Red No. 12, the strontium lake D&C Red No. 13, the aluminium lakes of FD&C Yellow No. 5, of FD&C Yellow No. 6, of D&C Red No. 27, of D&C Red No. 21, of FD&C Blue No. 1, iron oxides, manganese violet, chromium oxide and ultramarine blue.

Among the nail varnish pigments the most commonly used, mention may be made of D&C Red Nos. 8, 10, 30 and 36, the barium lakes of D&C Red Nos. 6, 9 and 12, the calcium lakes of D&C Red Nos. 7, 11, 31 and 34, the strontium lake of D&C Red No. 30 and D&C Orange No. 17 and D&C Blue No. 6, these pigments generally being present in a proportion of between 0.01 and 2% relative to the total weight of the varnish composition.

The nail varnishes can also contain titanium dioxide in order to give the varnishes a certain amount of opacity, as well as certain iridescent substances such as guanine and thixotropic agents for preventing sedimentation of the pigments, such as modified montmorillonite clays such as, for example, Bentone 27, Bentone 34 or Bentone 38.

The composition of the invention may be used to apply the spider silk protein to the skin, nails, hair or mucous membranes, by contacting the composition with the skin, nails, hair or mucous membranes of a subject. Preferably, the inventive composition is used with human subjects.

Having generally described this invention, a further understanding can be obtained by reference to certain specific examples which are provided herein for purposes of illustration only and are not intended to be limiting unless otherwise specified.

EXAMPLES

Example 1: Shampoo

A shampoo is prepared by mixing together the following ingredients:

| | |
|---|---|
| Ammonium lauryl sulphate | 12 g (AM) |
| Sodium chloride | 1 g |
| Crosslinked polyacrylic acid sold under the name "Carbopol 980 ®" by Goodrich | 3 g (AM) |

-continued

| | |
|---|---|
| Hydroxyethylcellulose crosslinked with epichlorohydrin, quaternized with trimethylamine, sold under the name "Celquat SC 40 ®" by National Starch | 1 g (AM) |
| Spider silk protein | 3 g |
| NaOH, qs pH 5 | |
| Preserving agents, fragrance, qs | |
| Water, qs | 100 g |

Example 2: Conditioner composition

A conditioner composition is prepared by mixing together the following ingredients:

| | |
|---|---|
| Crosslinked trimethylethyl ammonium methacrylate chloride/acrylamide copolymer (42/58) as a 50% dispersion in oil, sold under the name "Salcare SC92 ®" by Allied Colloids | 2 g (AM) |
| Cetyl/stearyl alcohol mixture oxyethylenated with 30 mol of ethylene oxide | 2 g (AM) |
| Spider silk protein | 5 g |
| HCl, qs pH 6 | |
| Water, qs | 100 g |

Example 3: Leave-in hair care lotion

A haircare composition is prepared by mixing together the following ingredients:

| | |
|---|---|
| Acrylic acid/C10/C30 alkyl acrylate copolymer sold under the name "Carbopol 1392 ®" by Goodrich | 2 g (AM) |
| Spider silk protein | 2 g |
| Ethyl alcohol | 5 g |
| NaOH, qs pH 6 | |
| Water, qs | 100 g |

Example 4: Nail varnish

A nail varnish is prepared by mixing together the following ingredients:

| | |
|---|---|
| Nitrocellulose | 16 g |
| Acetyl tributyl citrate | 6 g |
| Toluenesulphonamide formaldehyde resin | 10 g |
| Bentonite clay | 1.5 g |
| Pigments | 1.5 g |
| Isopropyl alcohol | 3 g |
| Recombinant spider silk protein | 0.5 g |
| Solvents (ethyl acetate and butyl acetate) qs | 100 g |

Example 5: Foundation (water-in-oil emulsion)

A foundation is prepared by mixing together the following ingredients:

| | |
|---|---|
| Copolymer of cetyl dimethicone and dimethicone copolyol, sold under the name "Abil WE09 ®" by Goldschmidt | 5 g |
| Cyclomethicone | 15 g |
| Caprylic/capric triglyceride sold under the name "Miglyol 812 ®" by Hüls AG | 5 g |
| Bentone gel VS 38 (clay at 10% in cyclomethicone) | 10 g |
| Recombinant spider silk protein | 1 g |
| Preserving agents, qs | |
| Pigments | 7 g |
| Water, qs | 100 g |

AM = Active material

The mixture is prepared cold using a turbomixer and the silk protein is incorporated after emulsification, by stirring for 5 minutes.

Obviously, additional modifications and variations of the present invention are possible in light of the above teachings. It is therefore to be understood that within the scope of the appended claims, the invention may be practiced otherwise than as specifically described herein.

This application is based on French Patent Application Serial No. 98-01614, filed on Feb. 11, 1998, and incorporated herein by reference in its entirety.

What is claimed is:

1. A cosmetic or dermatological composition, comprising:
   (A) an effective amount of at least one natural or recombinant spider silk protein or an analog of a spider silk protein comprising an amino acid repeating unit of sequence (II):

[(GPG$_2$YGPGQ$_2$)$_a$(X')$_2$S(A)$_b$]$_p$ (SEQ ID NO: 12)   (II)

wherein
   X' is the amino acid sequence GPS or GPG;
   a is 2 or 3;
   b is an integer from 7 to 10;
   p is an integer such that the molecular weight of the protein is between 10 and 400 kDa; and
   (B) at least one cosmetic adjuvant selected from the group consisting of fillers, surfactants, UVA and/or UVB sunscreens, thixotropic agents, antioxidants, preserving agents, dyes, pigments, fragrances, thickeners, vitamins, hormones, moisturizers, wetting agents, anionic, nonionic or aniphoteric polymers, and cosmetic or dermatological active substances.

2. The composition of claim 1, wherein the spider silk protein has the amino acid sequence shown in FIG. 2 (SEQ ID NO: 2).

3. The composition of claim 1, which contains from about $10^{-4}$ to about 30% by weight of the spider silk protein, relative to the total weight of the composition.

4. The composition of claim 1, which is an anhydrous composition and contains 10 to 90% by weight, relative to the total weight of the composition, of a fatty phase, wherein the fatty phase contains at least one liquid, solid or semi-solid fatty substance.

5. The composition of claim 4, wherein the fatty substance is selected from the group consisting of isododecane, hydrogenated polyisobutene, squalane, isononyl isononanoate, cyclotetra- and -pentadimethicones, phenyltrimethicone, ethylene homopolymers, copolymers of ethylene and of at least one monomer represented by the formula:

CH$_2$=CH—R$_3$ wherein
   R$_3$ is an alkyl radical containing from 1 to 30 carbon atoms or an aryl or aralkyl radical,
   microcrystalline waxes, ozocerite, beeswax, candelilla wax, and arachidyl propionate.

6. The composition of claim 1, which is in the form of an oily gel, a compacted powder, a cast powder or a stick.

7. The composition of claim 6, wherein the stick is a lipstick containing at least one dye and/or pigment in a proportion of from 0.1 to 15% by weight relative to the total weight of the composition.

8. The composition of claim 3, which is in the form of a stable dispersion of water-in-oil or oil-in-water type, and comprises:
   (i) a fatty phase in a proportion of from 0.1 to 50% by weight relative to the total weight of the composition, wherein the fatty phase contains a natural or recombinant spider silk protein, or an analog thereof, in a proportion of from $10^{-4}$ to 30% by weight relative to the total weight of the composition,
   (ii) an aqueous phase in a proportion of from 50 to 98.9% by weight relative to the total weight of the composition, and
   (iii) at least one emulsifier in a proportion of from 1 to 10% by weight relative to the total weight of the composition.

9. The composition of claim 8, wherein the fatty phase contains at least one fatty substance selected from the group consisting of isododecane, hydrogenated polyisobutene, squalane, isononyl isononanoate, cyclotetra- and -pentadimethicones, phenyltrimethicone, ethylene homopolymers, copolymers of ethylene and of at least one monomer represented by the formula:

CH$_2$=CH—R$_3$ wherein
   R$_3$ is an alkyl radical containing from 1 to 30 carbon atoms or an aryl or aralkyl radical,
   microcrystalline waxes, ozocente, beeswax, candelilla wax, and arachidyl propionate.

10. The composition of claim 1, which is in the form of a colorless or colored nail varnish containing:
    (i) a spider silk protein in a proportion of from $10^{-4}$ to 30% by weight relative to the total weight of the varnish,
    (ii) a solvent mixture for varnishes, and
    (iii) a film-forming substance.

11. The composition of claim 10, wherein the solvent mixture is present in a proportion of from 55 to 90% by weight and the film-forming substance in a proportion of from 5 to 35% by weight relative to the total weight of the composition.

12. The composition of claim 1, which contains said natural or recombinant spider silk protein.

13. The composition of claim 1, which contains said analog of a spider silk protein.

14. A method of applying a spider silk protein or an analog of a spider silk protein to skin, nails, hair or mucous membranes, comprising applying a cosmetic or dermatological composition comprising an effective amount of at least one natural or recombinant spider silk protein or an analog of a spider silk protein comprising an amino acid repeating unit of sequence (II):

[(GPG$_2$YGPGQ$_2$)$_a$(X')$_2$S(A)$_b$]$_p$ (SEQ ID NO: 12)   (II)

wherein
    X' is the amino acid sequence GPS or GPG;
    a is 2 or 3;
    b is an integer from 7 to 10;
    p is an integer such that the molecular weight of the protein is between 10 and 400 kDa,
    to skin, nails, hair or mucous membranes.

15. The method of claim 14, wherein the spider silk protein has the amino acid sequence shown in FIG. 2 (SEQ ID NO: 2).

16. The method of claim 14, wherein the composition contains from about $10^{-4}$ to about 30% by weight of the spider silk protein, relative to the total weight of the composition.

17. The method of claim 14, wherein the composition is an anhydrous composition and contains 10 to 90% by weight, relative to the total weight of the composition, of a fatty phase, wherein the fatty phase contains at least one liquid, solid or semi-solid fatty substance.

18. The method of claim 17, wherein the fatty substance is selected from the group consisting of isododecane, hydrogenated polyisobutene, squalane, isononyl isononanoate, cyclotetra- and -pentadimethicones, phenyltrimethicone, ethylene homopolymers, copolymers of ethylene and of at least one monomer represented by the formula:

$$CH_2=CH-R_3$$

wherein

R$_3$ is an alkyl radical containing from 1 to 30 carbon atoms or an aryl or aralkyl radical, microcrystalline waxes, ozocerite, beeswax, candelilla wax, and arachidyl propionate.

19. The method of claim 14, wherein the composition is in the form of an oily gel, a compacted powder, a cast powder or a stick.

20. The method of claim 19, wherein the stick is a lipstick containing at least one dye and/or pigment in a proportion of from 0.1 to 15% by weight relative to the total weight of the composition.

21. The method of claim 14, wherein the composition is in the form of a stable dispersion of water-in-oil or oil-in-water type, and comprises:

(i) a fatty phase in a proportion of from 0.1 to 50% by weight relative to the total weight of the composition, wherein the fatty phase contains a natural or recombinant spider silk protein, or an analog thereof, in a proportion of from $10^{-4}$ to 30% by weight relative to the total weight of the composition, (ii) an aqueous phase in a proportion of from 50 to 98.9% by weight relative to the total weight of the composition, and (iii) at least one emulsifier in a proportion of from 1 to 10% by weight relative to the total weight of the composition.

22. The method of claim 21, wherein the fatty phase contains at least one fatty substance selected from the group consisting of isododecane, hydrogenated polyisobutene, squalane, isononyl isononanoate, cyclotetra- and -pentadimethicones, phenyltrimethicone, ethylene homopolyiners, copolymers of ethylene and of at least one monomer represented by the formula:

$$CH_2=CH-R_3$$

wherein

R$_3$ is an alkyl radical containing from 1 to 30 carbon atoms or an aryl or aralkyl radical, microcrystalline waxes, ozocerite, beeswax, candelilla wax, and arachidyl propionate.

23. The method of claim 14, wherein the composition is in the form of a colorless or colored nail varnish containing:

(i) a spider silk protein in a proportion of from $10^{-4}$ to 30% by weight relative to the total weight of the varnish, (ii) a solvent mixture for varnishes, and (iii) a film-forming substance.

24. The method of claim 23, wherein the solvent mixture is present in a proportion of from 55 to 90% by weight and the film-forming substance in a proportion of from 5 to 35% by weight relative to the total weight of the composition.

25. The method of claim 24, wherein the composition further comprises at least one cosmetic adjuvant selected from the group consisting of fillers, surfactants, UVA and/or UVB sunscreens, thixotropic agents, antioxidants, preserving agents, dyes, pigments, fragrances, thickeners, vitamins, hormones, moisturizers, wetting agents, anionic, nonionic or amphoteric polymers, and cosmetic or dermatological active substances.

26. The method of claim 14, which contains said natural or recombinant spider silk protein.

27. The method of claim 14, which contains said analog of a spider silk protein.

28. An anhydrous cosmetic or dermatological composition, comprising:

(A) at least one natural or recombinant spider silk protein or an analog of a spider silk protein comprising an amino acid repeating unit of sequence (II):

$$[(GPG_2YGPGQ_2)_a(X')_2S(A)_b]_p \quad \text{(SEQ ID NO: 12)} \quad (II)$$

wherein

X' is the amino acid sequence GPS or GPG;

a is 2 or 3;

b is an integer from 7 to 10;

p is an integer such that the molecular weight of the protein is between 10 and 400 kDa; and (B) 10 to 90% by weight, relative to the total weight of the composition, of a fatty phase, wherein the fatty phase contains at least one liquid, solid or semi-solid fatty substance.

29. The composition of claim 28, wherein the fatty substance is selected from the group consisting of isododecane, hydrogenated polyisobutene, squalane, isononyl isononanoate, cyclotetra- and -pentadimethicones, phenyltrimethicone, ethylene homopolymers, copolymers of ethylene and of at least one monomer represented by the formula:

$$CH_2=CH-R_3$$

wherein

R$_3$ is an alkyl radical containing from 1 to 30 carbon atoms or an aryl or aralkyl radical, microcrystalline waxes, ozocerite, beeswax, candelilla wax, and arachidyl propionate.

30. The composition of claim 28, wherein the spider silk protein has the amino acid sequence shown in FIG. 2 (SEQ ID NO: 2).

31. The composition of claim 28, which contains from about $10^{-4}$ to about 30% by weight the spider silk protein, relative to the total weight of the composition.

32. The composition of claim 28, which is an anhydrous composition and contains 10 to 90% by weight, relative to the total weight of the composition, of a fatty phase, wherein the fatty phase contains at least one liquid, solid or semi-solid fatty substance.

33. The composition of claim 32, wherein the fatty substance is selected from the group consisting of isododecane, hydrogenated polyisobutene, squalane, isononyl isononanoate, cyclotetra- and -pentadimethicones, phenyltrimethicone, ethylene homopolymers, copolymers of ethylene and of at least one monomer represented by the formula:

$$CH_2=CH-R_3$$

wherein

R$_3$ is an alkyl radical containing from 1 to 30 carbon atoms or an aryl or aralkyl radical, microcrystalline waxes, ozocerite, beeswax, candelilla wax, and arachidyl propionate.

34. The composition of claim 28, which is in the form of an oily gel, a compacted powder, a cast powder or a stick.

35. The composition of claim 34, wherein the stick is a lipstick containing at least one dye and/or pigment in a proportion of from 0.1 to 15% by weight relative to the total weight of the composition.

36. The composition of claim 31, which is in the form of a stable dispersion of water-in-oil or oil-in-water type, and comprises:

(i) a fatty phase in a proportion of from 0.1 to 50% by weight relative to the total weight of the composition, wherein the fatty phase contains a natural or recombinant spider silk protein, or an analog thereof, in a proportion of from $10^{-4}$ to 30% by weight relative to the total weight of the composition, (ii) an aqueous phase in a proportion of from 50 to 98.9% by weight relative to the total weight of the composition, and (iii) at least one emulsifier in a proportion of from 1 to 10% by weight relative to the total weight of the composition.

37. The composition of claim 36, wherein the fatty phase contains at least one fatty substance selected from the group consisting of isododecane, hydrogenated polyisobutene, squalane, isononyl isononanoate, cyclotetra- and -pentadimethicones, phenyltrixnethicone, ethylene homopolymers, copolymers of ethylene and of at least one monomer represented by the formula:

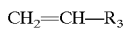

wherein $R_3$ is an alkyl radical containing from 1 to 30 carbon atoms or an aryl or aralkyl radical, microcrystalline waxes, ozocerite, beeswax, candelilla wax, and arachidyl propionate.

38. The composition of claim 28, which is in the form of a colorless or colored nail varnish containing:

(i) a spider silk protein in a proportion of from $10^{-4}$ to 30% by weight relative to the total weight of the varnish, (ii) a solvent mixture for varnishes, and (iii) a film-forming substance.

39. The composition of claim 38, wherein the solvent mixture is present in a proportion of from 55 to 90% by weight and the film-forming substance in a proportion of from 5 to 35% by weight relative to the total weight of the composition.

40. The composition of claim 28, further comprising at least one cosmetic adjuvant selected from the group consisting of fillers, surfactants, UVA and/or UVB sunscreens, thixotropic agents, antioxidants, preserving agents, dyes, pigments, fragrances, thickeners, vitamins, hormones, moisturizers, wetting agents, anionic, nonionic or amphoteric polymers, and cosmetic or dermatological active substances.

41. The composition of claim 28, which contains said natural or recombinant spider silk protein.

42. The composition of claim 28, which contains said analog of a spider silk protein.

43. A cosmetic or dermatological composition, comprising an effective amount of at least one natural or recombinant spider silk protein or an analog of a spider silk protein comprising an amino acid repeating unit of sequence (II):

$$[(GPG_2YGPGQ_2)_a(X')_2S(A)_b]_p \text{ (SEQ ID NO: 12)} \quad \text{(II)}$$

wherein

X' is the amino acid sequence GPS or GPG;

a is 2 or 3;

b is an integer from 7 to 10;

p is an integer such that the molecular weight of the protein is between 10 and 400 kDa, wherein the composition is in the form of an oily gel, a compacted powder, a cast powder, or a stick.

44. The composition of claim 43, wherein the stick is a lipstick containing at least one dye and/or pigment in a proportion of from 0.1 to 15% by weight relative to the total weight of the composition.

45. The composition of claim 43, wherein the spider silk protein has the amino acid sequence shown in FIG. 2 (SEQ ID NO: 2).

46. The composition of claim 43, which contains from about $10^{-4}$ to about 30% by weight of the spider silk protein, relative to the total weight of the composition.

47. The composition of claim 43, which is an anhydrous composition and contains 10 to 90% by weight, relative to the total weight of the composition, of a fatty phase, wherein the fatty phase contains at least one liquid, solid or semi-solid fatty substance.

48. The composition of claim 47, wherein the fatty substance is selected from the group consisting of isododecane, hydrogenated polyisobutene, squalane, isononyl isononanoate, cyclotetra- and -pentadimetbicones, phenyltrimethicone, ethylene homopolymers, copolymers of ethylene and of at least one monomer represented by the formula:

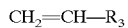

wherein $R_3$ is an alkyl radical containing from 1 to 30 carbon atoms or an aryl or aralkyl radical, microcrystalline waxes, ozocerite, beeswax, candelilla wax, and arachidyl propionate.

49. The composition of claim 43, which is in the form of an oily gel, a compacted powder, a cast powder or a stick.

50. The composition of claim 49, wherein the stick is a lipstick containing at least one dye and/or pigment in a proportion of from 0.1 to 15% by weight relative to the total weight of the composition.

51. The composition of claim 46, which is in the form of a stable dispersion of water-in-oil or oil-in-water type, and comprises:

(i) a fatty phase in a proportion of from 0.1 to 50% by weight relative to the total weight of the composition, wherein the fatty phase contains a natural or recombinant spider silk protein, or an analog thereof, in a proportion of from $10^{-4}$ to 30% by weight relative to the total weight of the composition, (ii) an aqueous phase in a proportion of from 50 to 98.9% by weight relative to the total weight of the composition, and (iii) at least one emulsifier in a proportion of from 1 to 10% by weight relative to the total weight of the composition.

52. The composition of claim 51, wherein the fatty phase contains at least one fatty substance selected from the group consisting of isododecane, hydrogenated polyisobutene, squalane, isononyl isononanoate, cyclotetra- and -pentadimethicones, phenyltrimethicone, ethylene homopolymers, copolymers of ethylene and of at least one monomer represented by the formula:

$$CH_2=CH-R_3$$

wherein $R_3$ is an alkyl radical containing from 1 to 30 carbon atoms or an aryl or aralkyl radical, microcrystalline waxes, ozocerite, beeswax, candelilla wax, and arachidyl propionate.

53. The composition of claim 43, which is in the form of a colorless or colored nail varnish containing:

(i) a spider silk protein in a proportion of from $10^{-4}$ to 30% by weight relative to the total weight of the varnish, (ii) a solvent mixture for varnishes, and (iii) a film-forming substance.

54. The composition of claim 53, wherein the solvent mixture is present in a proportion of from 55 to 90% by weight and the film-forming substance in a proportion of from 5 to 35% by weight relative to the total weight of the composition.

55. The composition of claim 43, further comprising at least one cosmetic adjuvant selected from the group consisting of fillers, surfactants, UVA and/or UVB sunscreens, thixotropic agents, antioxidants, preserving agents, dyes, pigments, fragrances, thickeners, vitamins, hormones, moisturizers, wetting agents, anionic, nonionic or aniphoteric polymers, and cosmetic or dei-matological active substances.

56. The composition of claim 43, which contains said natural or recombinant spider silk protein.

57. The composition of claim 43, which contains said analog of a spider silk protein.

58. A composition, wherein the composition is in the form of a stable dispersion of water-in-oil or oil-in-water type, and comprises:

(A) an effective amount of at least one natural or recombinant spider silk protein or an analog of a spider silk protein comprising an amino acid repeating unit of sequence (II):

$$[(GPG_2YGPGQ_2)_a(X')_2S(A)_b]_p \text{ (SEQ ID NO: 12)} \quad (II)$$

wherein

X' is the amino acid sequence GPS or GPG;

a is 2 or 3;

b is an integer from 7 to 10;

p is an integer such that the molecular weight of the protein is between 10 and 400 kDa;

(B) a fatty phase in a proportion of from 0.1 to 50% by weight relative to the total weight of the composition, wherein the fatty phase contains a natural or recombinant spider silk protein, or an analog thereof, in a proportion of from $10^{-4}$ to 30% by weight relative to the total weight of the composition;

(C) an aqueous phase in a proportion of from 50 to 98.9% by weight relative to the total weight of the composition; and (D) at least one emulsifier in a proportion of from 1 to 10% by weight relative to the total weight of the composition.

59. The composition of claim 58, wherein the fatty phase contains at least one fatty substance selected from the group consisting of isododecane, hydrogenated polyisobutene, squalane, isononyl isononanoate, cyclotetra- and -pentadimethicones, phenyltrimethicone, ethylene homopolymers, copolymers of ethylene and of at least one monomer represented by the formula:

$$CH_2=CH-R_3$$

wherein $R_3$ is an alkyl radical containing from 1 to 30 carbon atoms or an aryl or aralkyl radical, microcrystalline waxes, ozocerite, beeswax, candelilla wax, and arachidyl propionate.

60. The composition of claim 58, wherein the spider silk protein has the amino acid sequence shown in FIG. 2 (SEQ ID NO: 2).

61. The composition of claim 58, which contains from about $10^{-4}$ to about 30% by weight of the spider silk protein, relative to the total weight of the composition.

62. The composition of claim 58, which is an anhydrous composition and contains 10 to 90% by weight, relative to the total weight of the composition, of a fatty phase, wherein the fatty phase contains at least one liquid, solid or semi-solid fatty substance.

63. The composition of claim 62, wherein the fatty substance is selected from the group consisting of isododecane, hydrogenated polyisobutene, squalane, isononyl isononanoate, cyclotetra- and -pentadimethicones, phenyltrimethicone, ethylene homopolymers, copolymers of ethylene and of at least one monomer represented by the formula:

$$CH_2=CH-R_3$$

wherein $R_3$ is an alkyl radical containing from 1 to 30 carbon atoms or an aryl or aralkyl radical, microcrystalline waxes, ozocerite, beeswax, candelilla wax, and arachidyl propionate.

64. The composition of claim 58, which is in the form of an oily gel, a compacted powder, a cast powder or a stick.

65. The composition of claim 64, wherein the stick is a lipstick containing at least one dye and/or pigment in a proportion of from 0.1 to 15% by weight relative to the total weight of the composition.

66. The composition of claim 61, which is in the form of a stable dispersion of water-in-oil or oil-in-water type, and comprises:

(i) a fatty phase in a proportion of from 0.1 to 50% by weight relative to the total weight of the composition, wherein the fatty phase contains a natural or recombinant spider silk protein, or an analog thereof, in a proportion of from $10^{-4}$ to 30% by weight relative to the total weight of the composition, (ii) an aqueous phase in a proportion of from 50 to 98.9% by weight relative to the total weight of the composition, and (iii) at least one emulsifier in a proportion of from 1 to 10% by weight relative to the total weight of the composition.

67. The composition of claim 66, wherein the fatty phase contains at least one fatty substance selected from the group consisting of isododecane, hydrogenated polyisobutene, squalane, isononyl isononanoate, cyclotetra- and -pentadimethicones, phenyltrimethicone, ethylene homopolymers, copolymers of ethylene and of at least one monomer represented by the formula:

$$CH_2=CH-R_3$$

wherein
R_3 is an alkyl radical containing from 1 to 30 carbon atoms or an aryl or aralkyl radical,
microcrystalline waxes, ozocerite, beeswax, candelilla wax, and arachidyl propionate.

68. The composition of claim 58, which is in the form of a colorless or colored nail varnish containing:
  (i) a spider silk protein in a proportion of from $10^{-4}$ to 30% by weight relative to the total weight of the varnish,
  (ii) a solvent mixture for varnishes, and
  (iii) a film-forming substance.

69. The composition of claim 68, wherein the solvent mixture is present in a proportion of from 55 to 90% by weight and the film-forming substance in a proportion of from 5 to 35% by weight relative to the total weight of the composition.

70. The composition of claim 58, further comprising at least one cosmetic adjuvant selected from the group consisting of fillers, surfactants, UVA and/or UVB sunscreens, thixotropic agents, antioxidants, preserving agents, dyes, pigments, fragrances, thickeners, vitamins, hormones, moisturizers, wetting agents, anionic, nonionic or amphoteric polymers, and cosmetic or dermatological active substances.

71. The composition of claim 58, which contains said natural or recombinant spider silk protein.

72. The composition of claim 59, which contains said analog of a spider silk protein.

73. A composition, wherein the composition is in the form of a colorless or colored nail varnish, and comprises:
  (A) $10^{-4}$ to 30% by weight relative to the total weight of the composition of at least one natural or recombinant spider silk protein or an analog of a spider silk protein comprising an amino acid repeating unit of sequence (II):

$$[(GPG_2YGPGQ_2)_a(X')_2S(A)_b]_p \text{ (SEQ ID NO: 12)} \quad (II)$$

wherein
  X' is the amino acid sequence GPS or GPG;
  a is 2 or 3;
  b is an integer from 7 to 10;
  p is an integer such that the molecular weight of the protein is between 10 and 400 kDa;
  (B) a solvent mixture suitable for a nail varnish; and
  (C) a film-forming substance.

74. The composition of claim 73, wherein the solvent mixture is present in a proportion of from 55 to 90% by weight and the film-forming substance in a proportion of from 5 to 35% by weight relative to the total weight of the composition.

75. The composition of claim 73, wherein the spider silk protein has the amino acid sequence shown in FIG. 2 (SEQ ID NO: 2).

76. The cosmetic composition of claim 73, which contains from about $10^{-4}$ to about 30% by weight of the spider silk protein, relative to the total weight of the composition.

77. The composition of claim 73, which is an anhydrous composition and contains 10 to 90% by weight, relative to the total weight of the composition, of a fatty phase, wherein the fatty phase contains at least one liquid, solid or semi-solid fatty substance.

78. The composition of claim 73, wherein the fatty substance is selected from the group consisting of isododecane, hydrogenated polyisobutene, squalane, isononyl isononanoate, cyclotetra- and -pentadimethicones, phenyltrimethicone, ethylene homopolymers, copolymers of ethylene and of at least one monomer represented by the formula:

$$CH_2=CH-R_3$$

wherein
R_3 is an alkyl radical containing from 1 to 30 carbon atoms or an aryl or aralkyl radical,
microcrystalline waxes, ozocerite, beeswax, candelilla wax, and arachidyl propionate.

79. The composition of claim 73, which is in the form of an oily gel, a compacted powder, a cast powder or a stick.

80. The composition of claim 79, wherein the stick is a lipstick containing at least one dye and/or pigment in a proportion of from 0.1 to 15% by weight relative to the total weight of the composition.

81. The composition of claim 76, which is in the form of a stable dispersion of water-in-oil or oil-in-water type, and comprises:
  (i) a fatty phase in a proportion of from 0.1 to 50% by weight relative to the total weight of the composition, wherein the fatty phase contains a natural or recombinant spider silk protein, or an analog thereof, in a proportion of from $10^{-4}$ to 30% by weight relative to the total weight of the composition,
  (ii) an aqueous phase in a proportion of from 50 to 98.9% by weight relative to the total weight of the composition, and
  (iii) at least one emulsifier in a proportion of from 1 to 10% by weight relative to the total weight of the composition.

82. The composition of claim 81, wherein the fatty phase contains at least one fatty substance selected from the group consisting of isododecane, hydrogenated polyisobutene, squalane, isononyl isononanoate, cyclotetra- and -pentadimethicones, phenyltrimethicone, ethylene homopolymers, copolymers of ethylene and of at least one monomer represented by the formula:

$$CH_2=CH-R_3$$

wherein
R_3 is an alkyl radical containing from 1 to 30 carbon atoms or an aryl or aralkyl radical,
microcrystalline waxes, ozocerite, beeswax, candelilla wax, and arachidyl propionate.

83. The composition of claim 73, which is in the form of a colorless or colored nail varnish containing:
  (i) a spider silk protein in a proportion of from $10^{-4}$ to 30% by weight relative to the total weight of the varnish,
  (ii) a solvent mixture for varnishes, and
  (iii) a film-forming substance.

84. The composition of claim 83, wherein the solvent mixture is present in a proportion of from 55 to 90% by weight and the film-forming substance in a proportion of from $10^{-4}$ to 35% by weight relative to the total weight of the composition.

85. The composition of claim 73, further comprising at least one cosmetic adjuvant selected from the group consisting of fillers, surfactants, UVA and/or UVB sunscreens, thixotropic agents, antioxidants, preserving agents, dyes, pigments, fragrances, thickeners, vitamins, hormones, moisturizers, wetting agents, anionic, nonionic or amphoteric polymers, and cosmetic or dermatological active substances.

86. The composition of claim 73, which contains said natural or recombinant spider silk protein.

87. The composition of claim 73, which contains said analog of a spider silk protein.

88. A method of applying a spider silk protein to skin, nails, hair or mucous membranes, comprising applying the composition of claim 1 to skin, nails, hair or mucous membranes.

89. A method of applying a spider silk protein to skin, nails, hair or mucous membranes, comprising applying the composition of claim 8 to skin, nails, hair or mucous membranes.

90. A method of applying a spider silk protein to skin, nails, hair or mucous membranes, comprising applying the composition of claim 43 skin, nails, hair or mucous membranes.

91. A method of applying a spider silk protein to skin, nails, hair or mucous membranes, comprising applying the composition of claim 58 to skin, nails, hair or mucous membranes.

92. A method of applying a spider silk protein to skin, nails, hair or mucous membranes, comprising applying the composition of claim 73 to skin, nails, hair or mucous membranes.

* * * * *

UNITED STATES PATENT AND TRADEMARK OFFICE
CERTIFICATE OF CORRECTION

PATENT NO. : 6,841,162 B2
DATED : January 11, 2005
INVENTOR(S) : Michel Phillippe et al.

It is certified that error appears in the above-identified patent and that said Letters Patent is hereby corrected as shown below:

Column 35,
Line 20, "aniphoteric" should read -- amphoteric --.

Column 36,
Line 15, "ozocente" should read -- ozocerite --.

Column 39,
Line 24, "phenyltrixnethicone" should read -- phenyltrimethicone --.

Column 40,
Line 29, "pentadimetbicones" should read -- pentadimethicones --.

Column 41,
Line 28, "aniphoteric" should read -- amophoteric --.
Line 29, "dei-matological" should read -- dermatological --.

Column 44,
Line 61, "$10^{-4}$" should read -- $10^{-5}$ --.

Signed and Sealed this

Tenth Day of May, 2005

JON W. DUDAS
*Director of the United States Patent and Trademark Office*

SEQUENCE LISTING

<160> NUMBER OF SEQ ID NOS: 14

<210> SEQ ID NO 1
<211> LENGTH: 651
<212> TYPE: PRT
<213> ORGANISM: Nephila clavipes

<400> SEQUENCE: 1

```
Gln Gly Ala Gly Ala Ala Ala Ala Ala Gly Gly Ala Gly Gln Gly
 1               5                  10                  15

Gly Tyr Gly Gly Leu Gly Gly Gln Gly Ala Gly Gln Gly Gly Tyr Gly
            20                  25                  30

Gly Leu Gly Gly Gln Gly Ala Gly Gln Gly Ala Gly Ala Ala Ala Ala
            35                  40                  45

Ala Ala Ala Gly Gly Ala Gly Gln Gly Gly Tyr Gly Gly Leu Gly Ser
        50                  55                  60

Gln Gly Ala Gly Arg Gly Gly Gln Gly Ala Gly Ala Ala Ala Ala Ala
65                  70                  75                  80

Ala Gly Gly Ala Gly Gln Gly Gly Tyr Gly Gly Leu Gly Ser Gln Gly
                85                  90                  95

Ala Gly Arg Gly Gly Leu Gly Gly Gln Gly Ala Gly Ala Ala Ala Ala
            100                 105                 110

Ala Ala Ala Gly Gly Ala Gly Gln Gly Gly Tyr Gly Gly Leu Gly Asn
            115                 120                 125

Gln Gly Ala Gly Arg Gly Gly Gln Gly Ala Ala Ala Ala Ala Ala Gly
        130                 135                 140

Gly Ala Gly Gln Gly Gly Tyr Gly Gly Leu Gly Ser Gln Gly Ala Gly
145                 150                 155                 160

Arg Gly Gly Leu Gly Gly Gln Gly Ala Gly Ala Ala Ala Ala Ala Ala
                165                 170                 175

Gly Gly Ala Gly Gln Gly Gly Tyr Gly Gly Leu Gly Gly Gln Gly Ala
            180                 185                 190

Gly Gln Gly Gly Tyr Gly Gly Leu Gly Ser Gln Gly Ala Gly Arg Gly
        195                 200                 205

Gly Leu Gly Gly Gln Gly Ala Gly Ala Ala Ala Ala Ala Ala Ala Gly
    210                 215                 220

Gly Ala Gly Gln Gly Gly Leu Gly Gly Gln Gly Ala Gly Gln Gly Ala
225                 230                 235                 240

Gly Ala Ser Ala Ala Ala Ala Gly Gly Ala Gly Gln Gly Gly Tyr Gly
                245                 250                 255

Gly Leu Gly Ser Gln Gly Ala Gly Arg Gly Gly Glu Gly Ala Gly Ala
            260                 265                 270

Ala Ala Ala Ala Ala Gly Gly Ala Gly Gln Gly Gly Tyr Gly Gly Leu
        275                 280                 285

Gly Gly Gln Gly Ala Gly Gln Gly Gly Tyr Gly Gly Leu Gly Ser Gln
    290                 295                 300

Gly Ala Gly Arg Gly Gly Leu Gly Gly Gln Gly Ala Gly Ala Ala Ala
305                 310                 315                 320

Ala Gly Gly Ala Gly Gln Gly Gly Leu Gly Gly Gln Gly Ala Gly Gln
                325                 330                 335
```

```
Gly Ala Gly Ala Ala Ala Ala Ala Gly Gly Ala Gly Gln Gly Gly
            340                 345                 350

Tyr Gly Gly Leu Gly Ser Gln Gly Ala Gly Arg Gly Gly Leu Gly Gly
        355                 360                 365

Gln Gly Ala Gly Ala Val Ala Ala Ala Ala Gly Gly Ala Gly Gln
    370                 375                 380

Gly Gly Tyr Gly Gly Leu Gly Ser Gln Gly Ala Gly Arg Gly Gly Gln
385                 390                 395                 400

Gly Ala Gly Ala Ala Ala Ala Gly Gly Ala Gly Gln Arg Gly
        405                 410                 415

Tyr Gly Gly Leu Gly Asn Gln Gly Ala Gly Arg Gly Gly Leu Gly Gly
        420                 425                 430

Gln Gly Ala Gly Ala Ala Ala Ala Ala Gly Gly Ala Gly Gln
    435                 440                 445

Gly Gly Tyr Gly Gly Leu Gly Asn Gln Gly Ala Gly Arg Gly Gly Gln
    450                 455                 460

Gly Ala Ala Ala Ala Gly Gly Ala Gly Gln Gly Gly Tyr Gly Gly
465                 470                 475                 480

Leu Gly Ser Gln Gly Ala Gly Arg Gly Gly Gln Gly Ala Gly Ala Ala
                485                 490                 495

Ala Ala Ala Val Gly Ala Gly Gln Glu Gly Ile Arg Gly Gln Gly
            500                 505                 510

Ala Gly Gln Gly Gly Tyr Gly Gly Leu Gly Ser Gln Gly Ser Gly Arg
        515                 520                 525

Gly Gly Leu Gly Gly Gln Gly Ala Gly Ala Ala Ala Ala Ala Gly
    530                 535                 540

Gly Ala Gly Gln Gly Gly Leu Gly Gly Gln Gly Ala Gly Gln Gly Ala
545                 550                 555                 560

Gly Ala Ala Ala Ala Ala Gly Gly Val Arg Gln Gly Gly Tyr Gly
            565                 570                 575

Gly Leu Gly Ser Gln Gly Ala Gly Arg Gly Gly Gln Gly Ala Gly Ala
            580                 585                 590

Ala Ala Ala Ala Gly Gly Ala Gly Gln Gly Gly Tyr Gly Gly Leu
        595                 600                 605

Gly Gly Gln Gly Val Gly Arg Gly Gly Leu Gly Gly Gln Gly Ala Gly
    610                 615                 620

Ala Ala Ala Ala Gly Gly Ala Gly Gln Gly Gly Tyr Gly Gly Val Gly
625                 630                 635                 640

Ser Gly Ala Ser Ala Ala Ser Ala Ala Ala Ala
                645                 650

<210> SEQ ID NO 2
<211> LENGTH: 529
<212> TYPE: PRT
<213> ORGANISM: Nephila clavipes

<400> SEQUENCE: 2

Pro Gly Gly Tyr Gly Pro Gly Gln Gln Gly Pro Gly Gly Tyr Gly Pro
  1               5                  10                  15

Gly Gln Gln Gly Pro Ser Gly Pro Gly Ser Ala Ala Ala Ala Ala
                20                  25                  30

Ala Ala Ala Ala Gly Pro Gly Gly Tyr Gly Pro Gly Gln Gln Gly Pro
            35                  40                  45

Gly Gly Tyr Gly Pro Gly Gln Gln Gly Pro Gly Arg Tyr Gly Pro Gly
```

-continued

```
             50                  55                  60
Gln Gln Gly Pro Ser Gly Pro Gly Ser Ala Ala Ala Ala Ala Gly
 65                  70                  75                  80

Ser Gly Gln Gln Gly Pro Gly Gly Tyr Gly Pro Arg Gln Gln Gly Pro
                 85                  90                  95

Gly Gly Tyr Gly Gln Gly Gln Gln Gly Pro Ser Gly Pro Gly Ser Ala
                100                 105                 110

Ala Ala Ala Ser Ala Ala Ala Ser Ala Glu Ser Gly Pro Gly Gly
                115                 120                 125

Tyr Gly Pro Gly Gln Gln Gly Pro Gly Gly Tyr Gly Pro Gly Gln Gln
 130                 135                 140

Gly Pro Gly Gly Tyr Gly Pro Gly Gln Gln Gly Pro Ser Gly Pro Gly
145                 150                 155                 160

Ser Ala Ala Ala Ala Ala Ala Ala Ser Gly Pro Gly Gln Gln Gly
                165                 170                 175

Pro Gly Gly Tyr Gly Pro Gly Gln Gln Gly Pro Gly Gly Tyr Gly Pro
                180                 185                 190

Gly Gln Gln Gly Pro Ser Gly Pro Gly Ser Ala Ala Ala Ala Ala
                195                 200                 205

Ala Ala Ser Gly Pro Gly Gln Gln Gly Pro Gly Gly Tyr Gly Pro Gly
 210                 215                 220

Gln Gln Gly Pro Gly Gly Tyr Gly Pro Gly Gln Gln Gly Leu Ser Gly
225                 230                 235                 240

Pro Gly Ser Ala Ala Ala Ala Ala Ala Gly Pro Gly Gln Gln Gly
                245                 250                 255

Pro Gly Gly Tyr Gly Pro Gly Gln Gln Gly Pro Ser Gly Pro Gly Ser
                260                 265                 270

Ala Ala Ala Ala Ala Ala Ala Ala Gly Pro Gly Gly Tyr Gly Pro
                275                 280                 285

Gly Gln Gln Gly Pro Gly Gly Tyr Gly Pro Gly Gln Gln Gly Pro Ser
                290                 295                 300

Gly Ala Gly Ser Ala Ala Ala Ala Ala Ala Gly Pro Gly Gln Gln
305                 310                 315                 320

Gly Leu Gly Gly Tyr Gly Pro Gly Gln Gln Gly Pro Gly Gly Tyr Gly
                325                 330                 335

Pro Gly Gln Gln Gly Pro Gly Gly Tyr Gly Pro Gly Ser Ala Ser Ala
                340                 345                 350

Ala Ala Ala Ala Ala Gly Pro Gly Gln Gln Gly Pro Gly Gly Tyr Gly
                355                 360                 365

Pro Gly Gln Gln Gly Pro Ser Gly Pro Gly Ser Ala Ser Ala Ala Ala
 370                 375                 380

Ala Ala Ala Ala Ala Gly Pro Gly Gly Tyr Gly Pro Gly Gln Gln Gly
385                 390                 395                 400

Pro Gly Gly Tyr Ala Pro Gly Gln Gln Gly Pro Ser Gly Pro Gly Ser
                405                 410                 415

Ala Ser Ala Ala Ala Ala Ala Ala Ala Gly Pro Gly Gly Tyr Gly
                420                 425                 430

Pro Gly Gln Gln Gly Pro Gly Gly Tyr Ala Pro Gly Gln Gln Gly Pro
                435                 440                 445

Ser Gly Pro Gly Ser Ala Ala Ala Ala Ala Ala Ser Ala Gly Pro
                450                 455                 460

Gly Gly Tyr Gly Pro Ala Gln Gln Gly Pro Ser Gly Pro Gly Ile Ala
465                 470                 475                 480
```

-continued

```
Ala Ser Ala Ala Ser Ala Gly Pro Gly Tyr Gly Pro Ala Gln Gln
            485                 490                 495

Gly Pro Ala Gly Tyr Gly Pro Gly Ser Ala Val Ala Ala Ser Ala Gly
            500                 505                 510

Ala Gly Ser Ala Gly Tyr Gly Pro Gly Ser Gln Ala Ser Ala Ala Ala
            515                 520                 525

Ser

<210> SEQ ID NO 3
<211> LENGTH: 101
<212> TYPE: PRT
<213> ORGANISM: Nephila clavipes

<400> SEQUENCE: 3

Gly Ala Gly Arg Gly Gly Gln Gly Ala Gly Ala Ala Ala Ala Ala Ala
  1               5                  10                  15

Gly Gly Ala Gly Gln Gly Gly Tyr Gly Gly Leu Gly Ser Gln Gly Ala
             20                  25                  30

Gly Arg Gly Gly Leu Gly Gly Gln Gly Ala Gly Ala Ala Ala Ala Ala
         35                  40                  45

Ala Ala Gly Gly Ala Gly Gln Gly Gly Leu Gly Ser Gln Gly Ala Gly
     50                  55                  60

Gln Gly Ala Gly Ala Ala Ala Ala Ala Gly Gly Ala Gly Gln Gly
 65                  70                  75                  80

Gly Tyr Gly Gly Leu Gly Ser Gln Gly Ala Gly Gln Gly Gly Tyr Gly
                 85                  90                  95

Gly Leu Gly Ser Gln
            100

<210> SEQ ID NO 4
<211> LENGTH: 606
<212> TYPE: PRT
<213> ORGANISM: Nephila clavipes

<400> SEQUENCE: 4

Gly Ala Gly Arg Gly Gly Gln Gly Ala Gly Ala Ala Ala Ala Ala Ala
  1               5                  10                  15

Gly Gly Ala Gly Gln Gly Gly Tyr Gly Gly Leu Gly Ser Gln Gly Ala
             20                  25                  30

Gly Arg Gly Gly Leu Gly Gly Gln Gly Ala Gly Ala Ala Ala Ala Ala
         35                  40                  45

Ala Ala Gly Gly Ala Gly Gln Gly Gly Leu Gly Ser Gln Gly Ala Gly
     50                  55                  60

Gln Gly Ala Gly Ala Ala Ala Ala Ala Gly Gly Ala Gly Gln Gly
 65                  70                  75                  80

Gly Tyr Gly Gly Leu Gly Ser Gln Gly Ala Gly Gln Gly Gly Tyr Gly
                 85                  90                  95

Gly Leu Gly Ser Gln Gly Ala Gly Arg Gly Gly Gln Gly Ala Gly Ala
            100                 105                 110

Ala Ala Ala Ala Ala Gly Gly Ala Gly Gln Gly Gly Tyr Gly Gly Leu
        115                 120                 125

Gly Ser Gln Gly Ala Gly Arg Gly Gly Leu Gly Gly Gln Gly Ala Gly
    130                 135                 140

Ala Ala Ala Ala Ala Ala Ala Gly Gly Ala Gly Gln Gly Gly Leu Gly
145                 150                 155                 160
```

-continued

```
Ser Gln Gly Ala Gly Gln Gly Ala Gly Ala Ala Ala Ala Ala Gly
                165                 170                 175
Gly Ala Gly Gln Gly Gly Tyr Gly Gly Leu Gly Ser Gln Gly Ala Gly
                180                 185                 190
Gln Gly Gly Tyr Gly Gly Leu Gly Ser Gln Gly Ala Gly Arg Gly Gly
                195                 200                 205
Gln Gly Ala Gly Ala Ala Ala Ala Ala Gly Gly Ala Gly Gln Gly
        210                 215                 220
Gly Tyr Gly Gly Leu Gly Ser Gln Gly Ala Gly Arg Gly Gly Leu Gly
225                 230                 235                 240
Gly Gln Gly Ala Gly Ala Ala Ala Ala Ala Gly Gly Ala Gly
                245                 250                 255
Gln Gly Gly Leu Gly Ser Gln Gly Ala Gly Gln Gly Ala Gly Ala Ala
                260                 265                 270
Ala Ala Ala Ala Gly Gly Ala Gly Gln Gly Gly Tyr Gly Gly Leu Gly
        275                 280                 285
Ser Gln Gly Ala Gly Gln Gly Gly Tyr Gly Gly Leu Gly Ser Gln Gly
        290                 295                 300
Ala Gly Arg Gly Gly Gln Gly Ala Gly Ala Ala Ala Ala Ala Gly
305                 310                 315                 320
Gly Ala Gly Gln Gly Gly Tyr Gly Gly Leu Gly Ser Gln Gly Ala Gly
                325                 330                 335
Arg Gly Gly Leu Gly Gly Gln Gly Ala Gly Ala Ala Ala Ala Ala
                340                 345                 350
Ala Gly Gly Ala Gly Gln Gly Gly Leu Gly Ser Gln Gly Ala Gly Gln
        355                 360                 365
Gly Ala Gly Ala Ala Ala Ala Ala Gly Gly Ala Gly Gln Gly Gly
        370                 375                 380
Tyr Gly Gly Leu Gly Ser Gln Gly Ala Gly Gln Gly Gly Tyr Gly Gly
385                 390                 395                 400
Leu Gly Ser Gln Gly Ala Gly Arg Gly Gly Gln Gly Ala Gly Ala Ala
                405                 410                 415
Ala Ala Ala Ala Gly Gly Ala Gly Gln Gly Gly Tyr Gly Gly Leu Gly
        420                 425                 430
Ser Gln Gly Ala Gly Arg Gly Gly Leu Gly Gly Gln Gly Ala Gly Ala
        435                 440                 445
Ala Ala Ala Ala Ala Gly Gly Ala Gly Gln Gly Gly Leu Gly Ser
        450                 455                 460
Gln Gly Ala Gly Gln Gly Ala Gly Ala Ala Ala Ala Ala Gly Gly
465                 470                 475                 480
Ala Gly Gln Gly Gly Tyr Gly Gly Leu Gly Ser Gln Gly Ala Gly Gln
                485                 490                 495
Gly Gly Tyr Gly Gly Leu Gly Ser Gln Gly Ala Gly Arg Gly Gly Gln
                500                 505                 510
Gly Ala Gly Ala Ala Ala Ala Ala Gly Gly Ala Gly Gln Gly Gly
        515                 520                 525
Tyr Gly Gly Leu Gly Ser Gln Gly Ala Gly Arg Gly Gly Leu Gly Gly
        530                 535                 540
Gln Gly Ala Gly Ala Ala Ala Ala Ala Ala Gly Gly Ala Gly Gln
545                 550                 555                 560
Gly Gly Leu Gly Ser Gln Gly Ala Gly Gln Gly Ala Gly Ala Ala Ala
                565                 570                 575
Ala Ala Ala Gly Gly Ala Gly Gln Gly Gly Tyr Gly Gly Leu Gly Ser
```

```
                        580                 585                 590
Gln Gly Ala Gly Gln Gly Gly Tyr Gly Gly Leu Gly Ser Gln
            595                 600                 605

<210> SEQ ID NO 5
<211> LENGTH: 101
<212> TYPE: PRT
<213> ORGANISM: Nephila clavipes

<400> SEQUENCE: 5

Ser Gln Gly Ala Gly Gln Gly Gly Tyr Gly Gly Leu Gly Ser Gln Gly
  1               5                  10                  15

Ala Gly Arg Gly Gly Leu Gly Gly Gln Gly Ala Gly Ala Ala Ala Ala
             20                  25                  30

Ala Ala Ala Gly Gly Ala Gly Gln Gly Gly Leu Gly Ser Gln Gly Ala
         35                  40                  45

Gly Gln Gly Ala Gly Ala Ala Ala Ala Ala Gly Gly Ala Gly Gln
         50                  55                  60

Gly Gly Tyr Gly Gly Leu Gly Ser Gln Gly Ala Gly Arg Gly Gly Gln
 65                  70                  75                  80

Gly Ala Gly Ala Ala Ala Ala Ala Gly Gly Ala Gly Gln Gly Gly
             85                  90                  95

Tyr Gly Gly Leu Gly
            100

<210> SEQ ID NO 6
<211> LENGTH: 606
<212> TYPE: PRT
<213> ORGANISM: Nephila clavipes

<400> SEQUENCE: 6

Ser Gln Gly Ala Gly Gln Gly Gly Tyr Gly Gly Leu Gly Ser Gln Gly
  1               5                  10                  15

Ala Gly Arg Gly Gly Leu Gly Gly Gln Gly Ala Gly Ala Ala Ala Ala
             20                  25                  30

Ala Ala Ala Gly Gly Ala Gly Gln Gly Gly Leu Gly Ser Gln Gly Ala
         35                  40                  45

Gly Gln Gly Ala Gly Ala Ala Ala Ala Ala Gly Gly Ala Gly Gln
         50                  55                  60

Gly Gly Tyr Gly Gly Leu Gly Ser Gln Gly Ala Gly Arg Gly Gly Gln
 65                  70                  75                  80

Gly Ala Gly Ala Ala Ala Ala Ala Gly Gly Ala Gly Gln Gly Gly
             85                  90                  95

Tyr Gly Gly Leu Gly Ser Gln Gly Ala Gly Gln Gly Gly Tyr Gly Gly
            100                 105                 110

Leu Gly Ser Gln Gly Ala Gly Arg Gly Gly Leu Gly Gly Gln Gly Ala
        115                 120                 125

Gly Ala Ala Ala Ala Ala Ala Ala Gly Gly Ala Gly Gln Gly Gly Leu
    130                 135                 140

Gly Ser Gln Gly Ala Gly Gln Gly Ala Gly Ala Ala Ala Ala Ala Ala
145                 150                 155                 160

Gly Gly Ala Gly Gln Gly Gly Tyr Gly Gly Leu Gly Ser Gln Gly Ala
                165                 170                 175

Gly Arg Gly Gly Gln Gly Ala Gly Ala Ala Ala Ala Ala Ala Gly Gly
            180                 185                 190

Ala Gly Gln Gly Gly Tyr Gly Gly Leu Gly Ser Gln Gly Ala Gly Gln
```

```
            195                 200                 205
Gly Gly Tyr Gly Gly Leu Gly Ser Gln Gly Ala Gly Arg Gly Gly Leu
            210                 215                 220
Gly Gly Gln Gly Ala Gly Ala Ala Ala Ala Ala Ala Gly Gly Ala
225                 230                 235                 240
Gly Gln Gly Gly Leu Gly Ser Gln Gly Ala Gly Gln Gly Ala Gly Ala
                245                 250                 255
Ala Ala Ala Ala Ala Gly Gly Ala Gln Gly Gly Tyr Gly Gly Leu
            260                 265                 270
Gly Ser Gln Gly Ala Gly Arg Gly Gly Gln Gly Ala Gly Ala Ala Ala
            275                 280                 285
Ala Ala Ala Gly Gly Ala Gly Gln Gly Gly Tyr Gly Gly Leu Gly Ser
            290                 295                 300
Gln Gly Ala Gly Gln Gly Gly Tyr Gly Gly Leu Gly Ser Gln Gly Ala
305                 310                 315                 320
Gly Arg Gly Gly Leu Gly Gly Gln Gly Ala Ala Ala Ala Ala Ala
            325                 330                 335
Ala Ala Gly Gly Ala Gly Gln Gly Gly Leu Gly Ser Gln Gly Ala Gly
            340                 345                 350
Gln Gly Ala Gly Ala Ala Ala Ala Ala Gly Gly Ala Gly Gln Gly
            355                 360                 365
Gly Tyr Gly Gly Leu Gly Ser Gln Gly Ala Gly Arg Gly Gly Gln Gly
            370                 375                 380
Ala Gly Ala Ala Ala Ala Ala Gly Gly Ala Gly Gln Gly Gly Tyr
385                 390                 395                 400
Gly Gly Leu Gly Ser Gln Gly Ala Gly Gln Gly Gly Tyr Gly Gly Leu
            405                 410                 415
Gly Ser Gln Gly Ala Gly Arg Gly Gly Leu Gly Gly Gln Gly Ala Gly
            420                 425                 430
Ala Ala Ala Ala Ala Ala Gly Gly Ala Gly Gln Gly Gly Leu Gly
            435                 440                 445
Ser Gln Gly Ala Gly Gln Gly Ala Gly Ala Ala Ala Ala Ala Gly
            450                 455                 460
Gly Ala Gly Gln Gly Gly Tyr Gly Gly Leu Gly Ser Gln Gly Ala Gly
465                 470                 475                 480
Arg Gly Gly Gln Gly Ala Gly Ala Ala Ala Ala Ala Gly Gly Ala
            485                 490                 495
Gly Gln Gly Gly Tyr Gly Gly Leu Gly Ser Gln Gly Ala Gly Gln Gly
            500                 505                 510
Gly Tyr Gly Gly Leu Gly Ser Gln Gly Ala Gly Arg Gly Gly Leu Gly
            515                 520                 525
Gly Gln Gly Ala Gly Ala Ala Ala Ala Ala Ala Gly Gly Ala Gly
            530                 535                 540
Gln Gly Gly Leu Gly Ser Gln Gly Ala Gly Gln Gly Ala Gly Ala Ala
545                 550                 555                 560
Ala Ala Ala Ala Gly Gly Ala Gly Gln Gly Gly Tyr Gly Gly Leu Gly
                565                 570                 575
Ser Gln Gly Ala Gly Arg Gly Gly Gln Gly Ala Gly Ala Ala Ala Ala
                580                 585                 590
Ala Ala Gly Gly Ala Gly Gln Gly Gly Tyr Gly Gly Leu Gly
            595                 600                 605
```

<210> SEQ ID NO 7

<211> LENGTH: 101
<212> TYPE: PRT
<213> ORGANISM: Nephila clavipes

<400> SEQUENCE: 7

```
Gly Ala Gly Gln Gly Gly Tyr Gly Gly Leu Gly Ser Gln Gly Ala Gly
 1               5                  10                  15
Arg Gly Gly Leu Gly Gly Gln Gly Ala Gly Ala Ala Ala Ala Ala Ala
             20                  25                  30
Ala Gly Gly Ala Gly Gln Gly Gly Leu Gly Ser Gln Gly Ala Gly Gln
         35                  40                  45
Gly Ala Gly Ala Ala Ala Ala Ala Gly Gly Ala Gly Gln Gly Gly
     50                  55                  60
Tyr Gly Gly Leu Gly Ser Gln Gly Ala Gly Arg Gly Gly Gln Gly Ala
 65                  70                  75                  80
Gly Ala Ala Ala Ala Ala Gly Gly Ala Gly Gln Gly Gly Tyr Gly
                 85                  90                  95
Gly Leu Gly Ser Gln
            100
```

<210> SEQ ID NO 8
<211> LENGTH: 606
<212> TYPE: PRT
<213> ORGANISM: Nephila clavipes

<400> SEQUENCE: 8

```
Gly Ala Gly Gln Gly Gly Tyr Gly Gly Leu Gly Ser Gln Gly Ala Gly
 1               5                  10                  15
Arg Gly Gly Leu Gly Gly Gln Gly Ala Gly Ala Ala Ala Ala Ala Ala
             20                  25                  30
Ala Gly Gly Ala Gly Gln Gly Gly Leu Gly Ser Gln Gly Ala Gly Gln
         35                  40                  45
Gly Ala Gly Ala Ala Ala Ala Ala Gly Gly Ala Gly Gln Gly Gly
     50                  55                  60
Tyr Gly Gly Leu Gly Ser Gln Gly Ala Gly Arg Gly Gly Gln Gly Ala
 65                  70                  75                  80
Gly Ala Ala Ala Ala Ala Gly Gly Ala Gly Gln Gly Gly Tyr Gly
                 85                  90                  95
Gly Leu Gly Ser Gln Gly Ala Gly Gln Gly Gly Tyr Gly Gly Leu Gly
            100                 105                 110
Ser Gln Gly Ala Gly Arg Gly Gly Leu Gly Gly Gln Gly Ala Gly Ala
            115                 120                 125
Ala Ala Ala Ala Ala Gly Gly Ala Gly Gln Gly Gly Leu Gly Ser
        130                 135                 140
Gln Gly Ala Gly Gln Gly Ala Gly Ala Ala Ala Ala Ala Gly Gly
145                 150                 155                 160
Ala Gly Gln Gly Gly Tyr Gly Gly Leu Gly Ser Gln Gly Ala Gly Arg
                165                 170                 175
Gly Gly Gln Gly Ala Gly Ala Ala Ala Ala Ala Gly Gly Ala Gly
            180                 185                 190
Gln Gly Gly Tyr Gly Gly Leu Gly Ser Gln Gly Ala Gly Gln Gly Gly
            195                 200                 205
Tyr Gly Gly Leu Gly Ser Gln Gly Ala Gly Arg Gly Gly Leu Gly Gly
        210                 215                 220
Gln Gly Ala Gly Ala Ala Ala Ala Ala Ala Gly Gly Ala Gly Gln
225                 230                 235                 240
```

```
Gly Gly Leu Gly Ser Gln Gly Ala Gly Gln Gly Ala Gly Ala Ala Ala
            245                 250                 255

Ala Ala Ala Gly Gly Ala Gly Gln Gly Gly Tyr Gly Gly Leu Gly Ser
            260                 265                 270

Gln Gly Ala Gly Arg Gly Gly Gln Gly Ala Gly Ala Ala Ala Ala Ala
            275                 280                 285

Ala Gly Gly Ala Gly Gln Gly Gly Tyr Gly Gly Leu Gly Ser Gln Gly
            290                 295                 300

Ala Gly Gln Gly Gly Tyr Gly Gly Leu Gly Ser Gln Gly Ala Gly Arg
305                 310                 315                 320

Gly Gly Leu Gly Gly Gln Gly Ala Gly Ala Ala Ala Ala Ala Ala Ala
            325                 330                 335

Gly Gly Ala Gly Gln Gly Gly Leu Gly Ser Gln Gly Ala Gly Gln Gly
            340                 345                 350

Ala Gly Ala Ala Ala Ala Ala Gly Gly Ala Gly Gln Gly Gly Tyr
            355                 360                 365

Gly Gly Leu Gly Ser Gln Gly Ala Gly Arg Gly Gly Gln Gly Ala Gly
            370                 375                 380

Ala Ala Ala Ala Ala Gly Gly Ala Gly Gln Gly Gly Tyr Gly Gly
385                 390                 395                 400

Leu Gly Ser Gln Gly Ala Gly Gln Gly Gly Tyr Gly Gly Leu Gly Ser
            405                 410                 415

Gln Gly Ala Gly Arg Gly Gly Leu Gly Gly Gln Gly Ala Gly Ala Ala
            420                 425                 430

Ala Ala Ala Ala Ala Gly Gly Ala Gly Gln Gly Gly Leu Gly Ser Gln
            435                 440                 445

Gly Ala Gly Gln Gly Ala Gly Ala Ala Ala Ala Ala Gly Gly Ala
            450                 455                 460

Gly Gln Gly Gly Tyr Gly Gly Leu Gly Ser Gln Gly Ala Gly Arg Gly
465                 470                 475                 480

Gly Gln Gly Ala Gly Ala Ala Ala Ala Ala Gly Gly Ala Gly Gln
            485                 490                 495

Gly Gly Tyr Gly Gly Leu Gly Ser Gln Gly Ala Gly Gln Gly Gly Tyr
            500                 505                 510

Gly Gly Leu Gly Ser Gln Gly Ala Gly Arg Gly Gly Leu Gly Gly Gln
            515                 520                 525

Gly Ala Gly Ala Ala Ala Ala Ala Ala Gly Gly Ala Gly Gln Gly
            530                 535                 540

Gly Leu Gly Ser Gln Gly Ala Gly Gln Gly Gly Ala Ala Ala Ala
545                 550                 555                 560

Ala Ala Gly Gly Ala Gly Gln Gly Gly Tyr Gly Gly Leu Gly Ser Gln
            565                 570                 575

Gly Ala Gly Arg Gly Gly Gln Gly Ala Gly Ala Ala Ala Ala Ala
            580                 585                 590

Gly Gly Ala Gly Gln Gly Gly Tyr Gly Gly Leu Gly Ser Gln
            595                 600                 605

<210> SEQ ID NO 9
<211> LENGTH: 119
<212> TYPE: PRT
<213> ORGANISM: Nephila clavipes

<400> SEQUENCE: 9

Gly Pro Ser Gly Pro Gly Ser Ala Ala Ala Ala Ala Ala Gly Pro Gly
```

-continued

```
                1               5              10              15
Gln Gln Gly Pro Gly Gly Tyr Gly Pro Gly Gln Gln Gly Pro Gly Gly
                       20              25              30
Tyr Gly Pro Gly Gln Gln Gly Pro Ser Gly Pro Gly Ser Ala Ala Ala
                       35              40              45
Ala Ala Ala Ala Ala Gly Pro Gly Gly Tyr Gly Pro Gly Gln Gln Gly
                       50              55              60
Pro Gly Gly Tyr Gly Pro Gly Gln Gln Gly Pro Ser Gly Pro Gly Ser
 65                    70              75              80
Ala Ala Ala Ala Ala Ala Ala Ala Gly Pro Gly Gly Tyr Gly Pro
                       85              90              95
Gly Gln Gln Gly Pro Gly Gly Tyr Gly Pro Gly Gln Gln Gly Pro Gly
                      100             105             110
Gly Tyr Gly Pro Gly Gln Gln
                      115
```

<210> SEQ ID NO 10
<211> LENGTH: 714
<212> TYPE: PRT
<213> ORGANISM: Artificial Sequence
<220> FEATURE:
<223> OTHER INFORMATION: Description of Artificial Sequence:protein

<400> SEQUENCE: 10

```
Gly Pro Ser Gly Pro Gly Ser Ala Ala Ala Ala Ala Gly Pro Gly
 1               5              10              15
Gln Gln Gly Pro Gly Gly Tyr Gly Pro Gly Gln Gln Gly Pro Gly Gly
                       20              25              30
Tyr Gly Pro Gly Gln Gln Gly Pro Ser Gly Pro Gly Ser Ala Ala Ala
                       35              40              45
Ala Ala Ala Ala Ala Gly Pro Gly Gly Tyr Gly Pro Gly Gln Gln Gly
                       50              55              60
Pro Gly Gly Tyr Gly Pro Gly Gln Gln Gly Pro Ser Gly Pro Gly Ser
 65                    70              75              80
Ala Ala Ala Ala Ala Ala Ala Ala Gly Pro Gly Gly Tyr Gly Pro
                       85              90              95
Gly Gln Gln Gly Pro Gly Gly Tyr Gly Pro Gly Gln Gln Gly Pro Gly
                      100             105             110
Gly Tyr Gly Pro Gly Gln Gln Gly Pro Ser Gly Pro Gly Ser Ala Ala
                      115             120             125
Ala Ala Ala Ala Gly Pro Gly Gln Gln Gly Pro Gly Gly Tyr Gly Pro
 130                   135             140
Gly Gln Gln Gly Pro Gly Gly Tyr Gly Pro Gly Gln Gln Gly Pro Ser
 145                   150             155             160
Gly Pro Gly Ser Ala Ala Ala Ala Ala Ala Gly Pro Gly Gly
                      165             170             175
Tyr Gly Pro Gly Gln Gln Gly Pro Gly Gly Tyr Gly Pro Gly Gln Gln
                      180             185             190
Gly Pro Ser Gly Pro Gly Ser Ala Ala Ala Ala Ala Ala Ala
                      195             200             205
Gly Pro Gly Gly Tyr Gly Pro Gly Gln Gln Gly Pro Gly Gly Tyr Gly
                      210             215             220
Pro Gly Gln Gln Gly Pro Gly Gly Tyr Gly Pro Gly Gln Gln Gly Pro
 225                   230             235             240
Ser Gly Pro Gly Ser Ala Ala Ala Ala Ala Ala Gly Pro Gly Gln Gln
```

-continued

```
                245                 250                 255
Gly Pro Gly Gly Tyr Gly Pro Gly Gln Gln Gly Pro Gly Gly Tyr Gly
            260                 265                 270
Pro Gly Gln Gln Gly Pro Ser Gly Pro Gly Ser Ala Ala Ala Ala Ala
        275                 280                 285
Ala Ala Ala Gly Pro Gly Gly Tyr Gly Pro Gly Gln Gln Gly Pro Gly
    290                 295                 300
Gly Tyr Gly Pro Gly Gln Gln Gly Pro Ser Gly Pro Gly Ser Ala Ala
305                 310                 315                 320
Ala Ala Ala Ala Ala Ala Gly Pro Gly Gly Tyr Gly Pro Gly Gln
            325                 330                 335
Gln Gly Pro Gly Gly Tyr Gly Pro Gly Gln Gln Gly Pro Gly Gly Tyr
            340                 345                 350
Gly Pro Gly Gln Gln Gly Pro Ser Gly Pro Gly Ser Ala Ala Ala Ala
        355                 360                 365
Ala Ala Gly Pro Gly Gln Gln Gly Pro Gly Gly Tyr Gly Pro Gly Gln
    370                 375                 380
Gln Gly Pro Gly Gly Tyr Gly Pro Gly Gln Gln Gly Pro Ser Gly Pro
385                 390                 395                 400
Gly Ser Ala Ala Ala Ala Ala Ala Ala Gly Pro Gly Gly Tyr Gly
            405                 410                 415
Pro Gly Gln Gln Gly Pro Gly Gly Tyr Gly Pro Gly Gln Gln Gly Pro
        420                 425                 430
Ser Gly Pro Gly Ser Ala Ala Ala Ala Ala Ala Ala Ala Gly Pro
        435                 440                 445
Gly Gly Tyr Gly Pro Gly Gln Gln Gly Pro Gly Gly Tyr Gly Pro Gly
    450                 455                 460
Gln Gln Gly Pro Gly Gly Tyr Gly Pro Gly Gln Gln Gly Pro Ser Gly
465                 470                 475                 480
Pro Gly Ser Ala Ala Ala Ala Ala Ala Gly Pro Gly Gln Gln Gly Pro
            485                 490                 495
Gly Gly Tyr Gly Pro Gly Gln Gln Gly Pro Gly Gly Tyr Gly Pro Gly
            500                 505                 510
Gln Gln Gly Pro Ser Gly Pro Gly Ser Ala Ala Ala Ala Ala Ala
        515                 520                 525
Ala Gly Pro Gly Gly Tyr Gly Pro Gly Gln Gln Gly Pro Gly Gly Tyr
    530                 535                 540
Gly Pro Gly Gln Gln Gly Pro Ser Gly Pro Gly Ser Ala Ala Ala Ala
545                 550                 555                 560
Ala Ala Ala Ala Ala Gly Pro Gly Gly Tyr Gly Pro Gly Gln Gln Gly
            565                 570                 575
Pro Gly Gly Tyr Gly Pro Gly Gln Gln Gly Pro Gly Gly Tyr Gly Pro
            580                 585                 590
Gly Gln Gln Gly Pro Ser Gly Pro Gly Ser Ala Ala Ala Ala Ala Ala
        595                 600                 605
Gly Pro Gly Gln Gln Gly Pro Gly Gly Tyr Gly Pro Gly Gln Gln Gly
    610                 615                 620
Pro Gly Gly Tyr Gly Pro Gly Gln Gln Gly Pro Ser Gly Pro Gly Ser
625                 630                 635                 640
Ala Ala Ala Ala Ala Ala Ala Gly Pro Gly Gly Tyr Gly Pro Gly
            645                 650                 655
Gln Gln Gly Pro Gly Gly Tyr Gly Pro Gly Gln Gln Gly Pro Ser Gly
            660                 665                 670
```

```
Pro Gly Ser Ala Ala Ala Ala Ala Ala Ala Gly Pro Gly Gly
        675                 680                 685

Tyr Gly Pro Gly Gln Gln Gly Pro Gly Tyr Gly Pro Gly Gln Gln
        690                 695                 700

Gly Pro Gly Gly Tyr Gly Pro Gly Gln Gln
705                 710

<210> SEQ ID NO 11
<211> LENGTH: 15
<212> TYPE: PRT
<213> ORGANISM: Artificial Sequence
<220> FEATURE:
<223> OTHER INFORMATION: Xaa at position 1,4, and 8 corresponds to
      tyrosine or glutamine
<223> OTHER INFORMATION: Description of Artificial Sequence:protein

<400> SEQUENCE: 11

Xaa Gly Gly Xaa Gly Ala Gly Xaa Gly Ala Gly Ala Gly Ala Gly
 1               5                  10                  15

<210> SEQ ID NO 12
<211> LENGTH: 11
<212> TYPE: PRT
<213> ORGANISM: Artificial Sequence
<220> FEATURE:
<223> OTHER INFORMATION: Xaa corresponds to the amino acid sequence
      GPS or GPG
<223> OTHER INFORMATION: Description of Artificial Sequence:protein

<400> SEQUENCE: 12

Gly Pro Gly Tyr Gly Pro Gly Gln Xaa Ser Ala
 1               5                  10

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence:protein
<223> OTHER INFORMATION: Xaa corresponds to tyrosine, glutamine or
      alanine

<400> SEQUENCE: 13

Gly Arg Gly Ala Ala Gly Gly Xaa Gly Ala Ala
 1               5                  10

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence:protein
<223> OTHER INFORMATION: Xaa corresponds to tyrosine, glutamine,
      or alanine

<400> SEQUENCE: 14

Gly Gly Xaa Gly Ala Ala
 1               5
```